United States Patent [19]
Parenteau et al.

[11] Patent Number: 5,712,163
[45] Date of Patent: Jan. 27, 1998

[54] CHEMICALLY DEFINED CELL CULTURE MEDIA AND SYSTEM AND METHODS FOR USE, PARTICULARLY FOR CULTURING EPITHELIAL CELLS

[75] Inventors: Nancy Louise Parenteau, Brighton; Eric William Johnson, Malden; Susan Frances Meunier, Brighton; John Gregory Maresh, Cambridge, all of Mass.

[73] Assignee: Organogenesis, Inc., Canton, Mass.

[21] Appl. No.: 412,982

[22] Filed: Mar. 28, 1995

Related U.S. Application Data

[63] Continuation of Ser. No. 990,814, Dec. 14, 1992, abandoned, which is a continuation of Ser. No. 532,257, Jun. 1, 1990, abandoned, which is a continuation-in-part of Ser. No. 361,041, Jun. 5, 1989, abandoned.

[51] Int. Cl.[6] ..................... C12N 5/00
[52] U.S. Cl. .............. 435/405; 435/404; 435/366; 435/371; 435/384; 435/325
[58] Field of Search .............. 435/240.3, 240.31, 435/240.2, 240.23, 404, 405, 366, 371, 384, 325

[56] References Cited

U.S. PATENT DOCUMENTS

| | | | |
|---|---|---|---|
| 4,254,226 | 3/1981 | Eisinger et al. | 435/240 |
| 4,443,546 | 4/1984 | Stemerman et al. | 435/240.31 |
| 4,456,687 | 6/1984 | Green | 435/240.25 |
| 4,560,655 | 12/1985 | Baker | 435/241 |
| 4,673,649 | 6/1987 | Boyce et al. | 435/240.2 |
| 4,769,317 | 9/1988 | Hefton et al. | 435/1 |
| 4,885,238 | 12/1989 | Reddel et al. | 435/240.31 |
| 4,940,666 | 7/1990 | Boyce et al. | |
| 5,292,655 | 3/1994 | Wille, Jr. | 435/240.2 |

FOREIGN PATENT DOCUMENTS

| | | |
|---|---|---|
| 285471 | 10/1988 | European Pat. Off. |
| 285474 | 10/1988 | European Pat. Off. |
| 2 127 845 | 4/1984 | United Kingdom. |
| WO 89/09258 | 10/1989 | WIPO. |
| WO 90/07007 | 6/1990 | WIPO. |

OTHER PUBLICATIONS

Peehl and Ham, *In Vitro*, 16(1980)526–538.
Boyce and Ham, *J. Tiss. Cult. Meth.*, 9(1985)83–93.
Pitelkow and Scott, *Mayo Clin. Proc.*, 61(1986)771–777.
Rice and Green, *Cell*, vol. 18, 681–694.
Karasek and Charlton, *J. Invest. Dermatol.*, 56(1971)205–210.
Gilchrest et al., *J. Cell Physiol.*, 112(197–206) (1982).
Gilchrest et al., *Cell Biol. Int'l Rpt.*, 4(1980)1009–1016.
Eisenger et al., *Proc. Nat'l Aca. Sci.*, 76(1976)5340–5344.
Barrandon and Green, *Cell*, 50(1987)1131–1137.
Bertolero et al., *Exp. Cell Res.*, 155(1984)64–80.
Gilchrest et al., *J. Cell Phys.*, 120(1984)377–383.
O'Keefe and Chiu, *Soc. Invest. Dermatol.*, 90(1988)2–7.
Liu et al., *In Vitro*, 15(1979)813–822.
Kubo et al., *Soc. Invest. Dermatol.*, 88(1987)594–601.
W. Imagawa et al., *Proc. Natl. Acad. Sci.*, "Serum–free growth of normal and tumor mouse mammary epithelial cells in primary culture", 79:4074–4077, (Jul. 1982).
M.C. Tsao et al., *Journal of Cellular Physiology*, "Clonal Growth of Normal Human Epidermal Keratinocytes in a Defined Medium", 110:219–229 (1982).
Gilchrest, et al. Attachment and Growth of Human Keratinocytes in a Serum–Free Environment J. Cellular Physiology vol. 112, pp. 197–206 1982.
Gilchrest, et al. Characterization and Partial Purification of Keratinocyte Growth Factor From the Hypothalamus J. Cellular Physiology vol. 120, pp. 377–383 1984.
Boyce, et al. Cultivation, Frozen Storage and Clonal Growth of Normal Human Epidermal Keratinocytes in Serum–Free Media J. Tissue Culture Methods vol. 9 No. 2, pp. 83–93 1985.
Kubo, et al. Effects of Extracellular Matrices on Human Keratinocyte Adhesion and Growth and on its Secretion and Deposition . . . J. Investigative Dermatology vol. 88 No. 5, pp. 594–601 1987.
Barrandon, Y. et al., "Cell Size as a Determinant of the Clone–forming Ability of Human Keratinocytes," *Cell Biology*, vol. 82, pp. 5390–5394, Aug. 1985.
Breidahl, A.F. et al., "Review of Keratinocyte Culture Techniques: Problems of Growing Skin," Aust. N.J. Surg., 1989, vol. 59, pp. 485–497.
Vollberg, T. et al., "Induction of Extracellular Matrix Gene Expression in Normal Keratinocytes . . ." Experimental Cell Research, vol. 193, 93–100 (1991).

*Primary Examiner*—John W. Rollins
*Assistant Examiner*—Christopher R. Tate
*Attorney, Agent, or Firm*—David G. Conlin; Linda M. Buckley

[57] ABSTRACT

The present invention provides systems, methods and chemically defined media for the cultivation of cells, particularly epithelial cells. Cells may be cultured with a varied calcium concentration. Furthermore, a calcium concentation in excess of 1.00 mM may be used in the practice of the present invention without loss of a proliferative cell population and maintianing high colony forming efficiencies. Population doubling times range from about 16 to about 33 hours. Cells may serially cultivated to achieve from about 20 to about 50 population doublings.

27 Claims, 2 Drawing Sheets

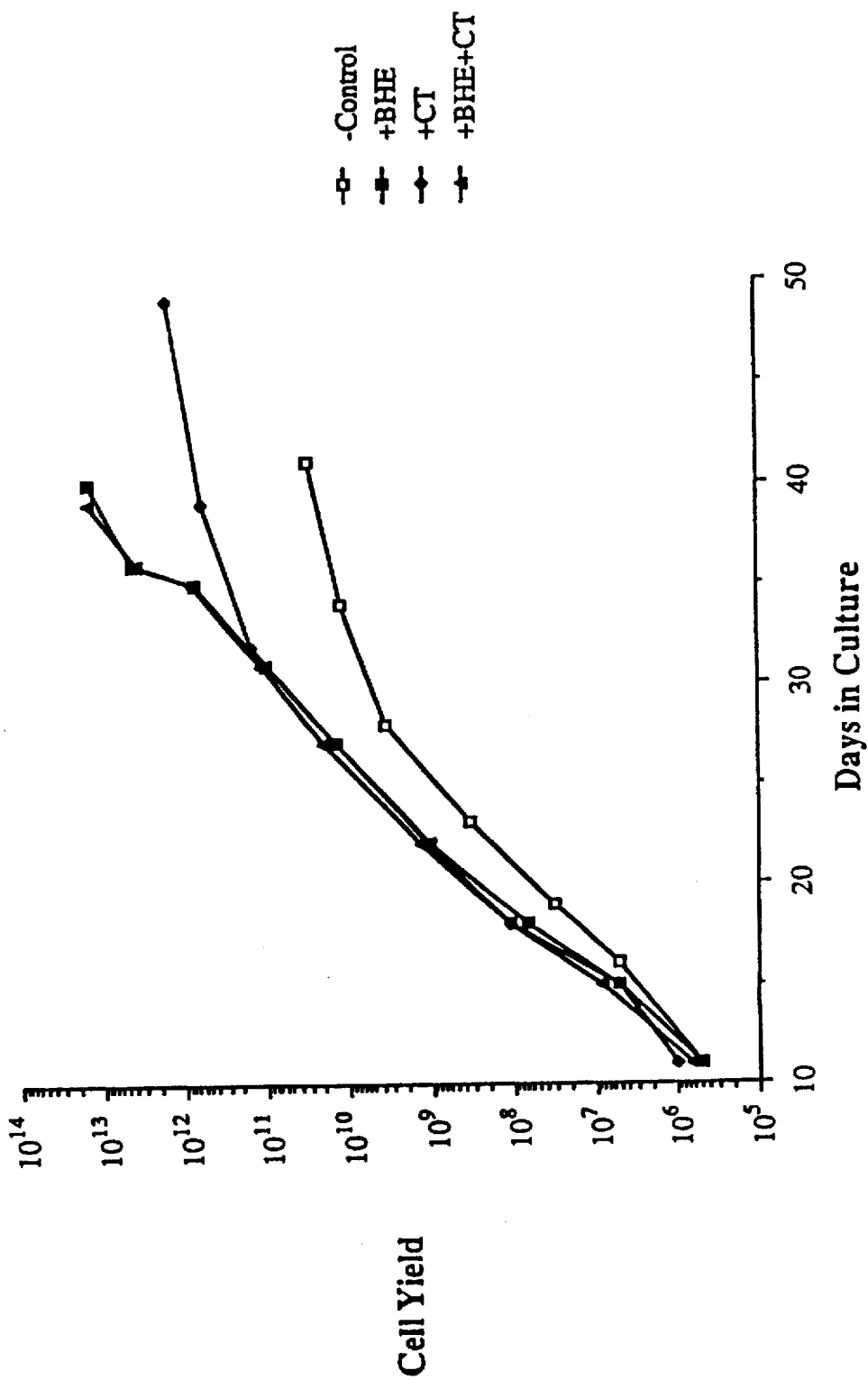

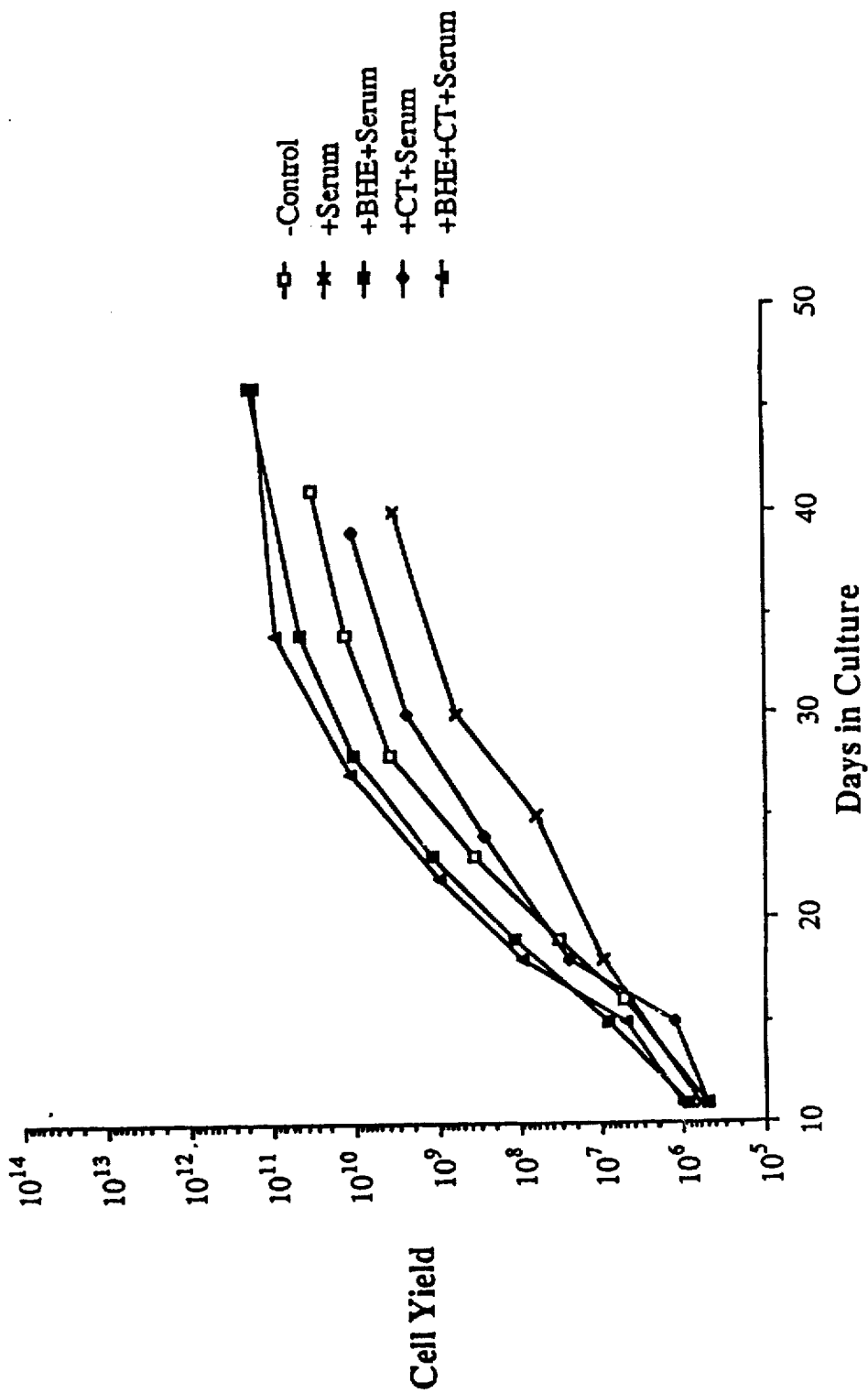

CHEMICALLY DEFINED CELL CULTURE MEDIA AND SYSTEM AND METHODS FOR USE, PARTICULARLY FOR CULTURING EPITHELIAL CELLS

BACKGROUND OF THE INVENTION

This is a continuation of application Ser. No. 07/990,814 filed on Dec. 14, 1992* now abandoned, which is a continuation-in-part of application Ser. No. 07/361,041, filed Jun. 5, 1989 now abandoned.

* which is a file wrapper continuation application of Ser. No. 07/532,257, filed Jun. 1, 1990, now abandoned.

This invention relates to media and systems for cell growth and to methods of making and using such media and systems.

At present most media or systems for prolonged or long term growth and proliferation of normal mammalian cells incorporate undefined proteins or use feeder cells to provide proteins necessary to sustain such growth and proliferation.

Because the presence of such undefined proteins can interfere with the intended end use of the cultured cells, it is desirable that cells be cultured under conditions to minimize the presence of undefined proteins. By way of example, it is anticipated that the presence of undefined proteins in cultured epidermal cells which are used to prepare living skin equivalents for use as skin grafts for burn victims may make such living skin equivalents unsuitable for this use, because such proteins may provoke an immune reaction. If mouse 3T3 feeder cells are used to culture epidermal cells for such living skin equivalents, it is highly likely that residual 3T3 cells or parts thereof trapped in the epidermis would cause a cross-species immune reaction. The use of bovine serum in fabrication of such living skin equivalents would be likely to produce a similar immune reaction.

Thus, there is a need for chemically defined cell culture media and systems which provide for the prolonged growth and proliferation of cells either at a very low concentration of undefined proteins, or, more preferably, in the absence of such undefined proteins. The term "defined" is used to describe medium that contains no deliberately added uncharacterized supplements, even though such a medium may contain trace contaminants in its components.

A wide variety of chemically defined culture media have been developed for the propagation of cells in response to this need. Such media include modified Eagles Medium (hereinafter "MEM"), Ham's F-12, Dulbeco's Modified Eagle's Medium (hereinafter "DMEM"), MCDB 153 and Medium 199. However, it has been found that successful culture of most cells in known chemically defined media still requires the addition of protein supplements such as serum or factors derived from serum or the use of feeder cells, thereby introducing undefined components to the media. Use of complex protein supplements in cell culture systems not only introduces undefined proteins but also increases the cost of cell culture.

Problems encountered in the culture and, in some cases, maturation of epithelial cells are illustrative of the deficiencies in presently available culture media and systems. Epithelial cells, such as epidermal cells, are used to fabricate living skin equivalents and to produce sheets of cultured epidermis for use in test systems and skin grafting. Living skin and other tissue equivalents and methods of making and using such tissue equivalents are disclosed in U.S. Pat. No. 4,485,096; U.S. Pat. No. 4,835,102; U.S. Pat. No. 4,837,379; U.S. Ser. No. 07/505,678, filed Apr. 6, 1990 now U.S. Pat. No. 5,256,418; and U.S. Ser. No. 07/408,052, filed Sep. 15, 1989 now abandoned; all of which are incorporated herein by reference, and referred to hereinafter as the "Patents." These applications require the growth of large quantities of epidermal cells in culture and presently available media do not meet this need.

The mammalian epidermis is composed principally of a single cell type, the keratinocyte, in various stages of differentiation. The basal layer, separated from the fibroblasts of the underlying dermis, contains the dividing keratinocytes. These give rise to progeny, some of which no longer divide but move outward from the basal layer, terminally differentiate to form the stratum corneum, and are eventually shed from the surface. For certain applications, e.g., test systems for studies on percutaneous absorption, it is essential that living skin equivalents include a fully developed keratinocyte layer which requires the differentiation and maturation of the cultured epidermal cells.

The formation of keratinocyte sheets, akin to those seen in vivo, presents additional challenges for existing cell growth media and systems. The formation of such sheets requires a calcium concentration sufficient to allow differentiation of the epidermal cells and to allow the stratification of older, more mature keratinocytes while still maintaining a proliferative, small basal cell population. The culture and maturation of keratinocytes has been attempted by various methods and with varying degrees of success, even when serum or protein supplements have been used. For example, it has been found that the growth requirements of keratinocytes are not met by conventional serum supplementation of chemically defined media. In any event, growth and maturation of keratinocytes is preferably achieved using a chemically defined culture media with little or no added serum or other undefined factors and without the use of feeder cells such as embryonic mouse fibroblasts (3T3 cells).

In reviewing current techniques for culturing keratinocytes, a number of problems come to light. See, e.g., Breidahl et al., *Aust. N.Z. J. Surg.*, 59(1989) 485–497.

Rheinwald and Green reported a method for growing keratinocytes using a 3T3 feeder cell layer which allowed clonal growth and multiple passage (Rheinwald and Green, *Cell* 6(1975)331–344). This work was considered a breakthrough methodology, because the keratinocyte cells were able to form stratifying, differentiating cultures which still maintained a proliferative or relatively undifferentiated basal cell population capable of further clonal growth when passaged. Notwithstanding the foregoing advantages of the Rheinwald and Green methodology, the use of feeder cells, e.g., mouse 3T3 cells, is undesirable because of the possibility that undefined proteins from the 3T3 cells, a transformed line, will be present in the cultured cells. Although it is reported (Sun and Green, *Cell*, 9(1976)512–521) that 3T3 cells and cell fragments may be removed by using 0.02% EDTA, complete removal is often difficult and the effect of removal of these cells and the resultant stress placed on the cultured epidermal cells is likely to be undesirable. Furthermore, the 3T3 feeder system requires high amounts of serum (about 5%), adding further undefined proteins to the culture system.

After the work of Rheinwald and Green, supra, researchers continued to try to find a way of culturing epidermal cells and maturing keratinocytes in the absence of supplement or feeder cell support. A major advancement in this area was reported by Boyce and Ham in *J. Invest. Dermatol.* 81(1983)33S–40S. This work began by using Ham's F-12 as a base medium supplemented with reduced amounts of dialyzed FBS (2%) (Peehl and Ham, *In Vitro* 16(1980)526–538). An optimized formulation of this medium which allowed the growth of keratinocytes in a serum-free medium containing reduced calcium was subsequently developed by changing the concentration of a number of components to arrive at a medium designated MCDB 153 (See Boyce and Ham 1983, supra, and *J. Tiss. Cult. Meth.* 9(1985)83–93).

The reported usefulness of MCDB 153 is in the areas of keratinocyte cell biology, toxicology, pathology and the growth of cells for epidermal cell grafts (Boyce and Ham 1985, supra). Although MCDB 153 is a serum free medium which does not require the use of feeder cells, it suffers certain disadvantages. For example, its use is limited in that MCDB 153 is not a very flexible medium, e.g., in the presence of calcium and/or serum.

The ability to cultivate keratinocytes in MCDB 153 is critically dependent on the calcium concentration of the medium further limiting its flexibility. Proliferative ability in MCDB 153 is maintained by keeping the calcium concentration below about 1.0 mM, about 0.3 mM being optimal (See Boyce and Ham 1983, FIG. 1, p. 35S, supra). When calcium is added to concentrations of about 1.0 mM or above in MCDB 153 to cause stratification, the cells will no longer divide, will terminally differentiate and will not be capable of further cultivation, i.e., the proliferating basal cell population is lost because the cells cannot withstand high calcium concentrations in this medium. (Boyce and Ham 1983, supra). Because, a physiological concentration of approximately 1.8 mM calcium is necessary for a proper stratification and differentiation of a coherent multilayered epidermal sheet, MCDB 153 is not an appropriate medium to achieve a fully developed keratinocyte layer. Pittelkow and Scott (*Mayo Clin. Proc.* 61 (1986) 771–777) report formed sheets of graftable epidermis using cells cultivated in MCDB 153 but found it necessary to return to a DMEM-high serum (10%) medium to achieve stratification and at the same time maintain adequate viability.

MCDB 153 is further limited in that cells grown in MCDB 153 dramatically lose their ability to be passaged if grown to confluence (Boyce and Ham 1983, supra). This finding indicates that the great majority of cells continue to differentiate even though the calcium concentration is kept below 1.0 mM and is possibly one reason why the MCDB 153 system is also so intolerant of calcium, since calcium is known to induce the final process of terminal differentiation in committed cells (Rice and Green, *Cell*, Vol 18, 681–694, November 1979). Furthermore, colony forming efficiencies of 30% and population doubling times of approximately 24 hours are achieved in MCDB 153 only at passages 2–3. These properties are seen to decline beyond passage 3 (Boyce and Ham 1983, supra).

It is believed that the quality of cells grown in MCDB 153 would not be sufficiently high for use in the fabrication of epidermal cell sheets and that statified cultures, which can be held at confluence for some period of time, cannot be achieved in the present MCDB 153 system.

Although other researchers working with a suboptimal medium tried to optimize their system by use of growth substrates (See, e.g., Karasek and Charlton (*J. Invest. Dermal,* 56(1971) 205–210), and Gilchrest et al. (*J. Cell Physiol.* 112 (1982) 197–206) reported the benefits of a protein substrate in culture of epidermal keratinocytes), these workers achieved only a limited degree of success, primarily due to deficiencies in medium formulation. Karasek and Charlton supra, and other researchers found it necessary to use a high serum concentration (usually around 10%). The supplemented M199 medium used by Gilchrest et al., (*Cell Biol. Intl. Rpt.,* 4(1980) 1009–1016), suffered a basic nutrient deficiency, i.e., a very low inositol concentration.

In Eisinger (*Methods in Skin Research,* Eds. Skerrow and Skerrow, Chap. 7, J. Wiley & Sons Ltd. 1985) and Eisenger et al. (*Proc. Natl Aca. Sci.* 76 (1979) 5340–5344) a method of growing epidermal cells is reported, the stated advantage of which is the growth of cells without feeder cells and without a dermal component. However, the Eisinger method, supra, relies on an extremely high cell density for plating. Furthermore, growth rate is slow and fold-increase in total cell number is low (partially due to a low plating efficiency), making this technique impractical for large scale expansion or prolonged cultivation from a single source, both desired objectives.

It is known to those skilled in the art that supplementation of base medium with epidermal growth factor and hydrocortisone enhances the growth and spreading of keratinocytes (Barrandon and Green *Cell* 50(1987)1131–1137; Bertolero et al., *Exp. Cell Res.* 155(1984)64–80). Cyclic AMP elevating agents (See, e.g., U.S. Pat. No. 4,456,687) and the use of bovine neural extract (Gilchrest et al., *J. Cell Phys.* 120 (1984) 377–383) or placental extract (O'Keefe and Chiu, *Soc. Invest, Dermatol.* 90 (1988) 2–7) are also of benefit in a number of cell culture systems.

A survey of the literature indicates that while a number of workers have attempted growth of epithelial cells with either a collagen substrate (Liu et al. *In Vitro* 15 (1979) 813–822) or fibronectin substrate (Kubo et al., *Soc. Invest, Dermatol.* 88 (1987) 594–601) or using various media formulations, for the most part only short term culture at relatively high seeding densities has been achieved. None of these modifications, including MCDB 153, approach the level of success seen using the 3T3 feeder cell system.

The 3T3, feeder system, however, requires the use of cAMP elevating agent, typically cholera toxin, in order to achieve optimal growth (Green, *Cell* 15 (1978) 801–811). This artificial elevation of cAMP levels complicates the study of actual growth factor effects and mechanisms.

Media and systems which provide for the prolonged growth and proliferation of cells, and in some instances maturation of certain cells while maintaining actively dividing basal cells, are being sought.

SUMMARY OF THE INVENTION

Cells grown in the cell culture media and systems of the present invention have a number of advantages including but not limited to:

1. Lack of feeder cell.
2. Rapid growth rate in the absence of serum and/or bovine hypothalmic extract.
3. If plated at about $1 \times 10^3$ cells/cm$^2$ or higher, use of bovine hypothalamic extract provides little or no advantage.
4. Rapid cell growth in the absence of cAMP elevating agents.
5. Plating and colony forming efficiency is 30% or higher with flexibility of the calcium concentration. This compares to approximately 10% with 3T3 and 30% with MCDB 153-low calcium. (This characteristic is highly desirable for microcarrier cultivation).
6. Cells may be easily used in the fabrication of living skin equivalents and form a multilayered epidermis as good or better than cells grown by other methods described (MCDB 153 grown cells do not survive well).
7. Epidermal cells grown on a collagen coated surface can be released as a sheet of epidermal cells using collagenase for use in transplantation of these sheets, if desired.

8. The flexibility of the systems in range of $Ca^{++}$ concentrations, serum requirements and density dependence provide, a number of advantages for adaptation to large scale microcarrier culture.
9. The rapid growth rate produces a nearly synchronous population of cells as they approach approximately 60% confluence. The large number of rounded mitotic cells and the high plating efficiency of cells grown in accordance with the present invention, indicates that bead to bead transfer may also be possible in large scale microcarrier culture.

BRIEF DESCRIPTION OF THE DRAWINGS

FIG. 1 are graphs showing the cell yield obtained in the absence of exogenous cAMP elevating agents and in the presence of BHE; of CTE; and of BHE and CT.

FIG. 2 are graphs showing the cell yield obtained in the absence of exogenous cAMP elevating agents and serum, and in the presence of serum; of serum and BHE; serum and CT; and of serum, BHE and CT.

Cell culture media in accordance with the present invention comprise, insulin or an insulin-like growth factor; ferrous ion; triiodothyronine or thyroxin; at least one of ethanolamine or o-phosphoryl-ethanolamine; calcium; and a nutrient source. A preferred medium in accordance with the present invention comprises:

(a) Insulin at from about 0.5 to about 50 ug/ml;
(b) Ferrous ion or transferrin at from about $5\times10^{-8}$ to about $5\times10^{-5}M$;
(c) Triiodothyronine at from about 2 to about 200 pM;
(d) At least one of o-phosphoryl-ethanolamine and ethanolamine at from about $10^{-6}$ to about $10^{-2}M$;
(e) Calcium at from about 0.005 to about 2.0 mM; and
(f) Nutrient Source selected from at least one of DMEM, IDMEM, MEM, M199, RPMI 1640, Ham's F12, Ham's F10, NCTC 109, and NCTC 135.

Other components which may be included in media in accordance with the present invention include hydrocortisone at from about 0.04 to about 4.0 ug/ml; Epidermal Growth Factor at from about 1 to about 50 ng/ml; adenine at from about 0.02 to 2 mM; chelexed serum at from about 0.05% to about 2.00%; progesterone at from about $2\times10^{-10}$ to about $2\times10^{-8}M$; selenium from about $10^{-9}$ to about $10^{-7}M$; Bovine Hypothalmic Extract from about $1\times10^{-5}$ to about $2\times10^{-4}$ g/ml; strontium at about $10^{-4}$ to about $2\times10^{-3}M$; one or more cAMP elevating agents at about $10^{-9}$ to $10^{-3}M$ selected from at least one of cholera toxin, foreskolin, isoproterenol, methyl isobutyl xanthine, dibutyrl c-AMP, theophylline, caffeine and pertussis toxin; EGF at from about 1 to about 50 ng/ml; and ferrous ion is supplied by ferric sulfate at from about $5\times10^{-8}$ to about $5\times10^{-5}M$. Ferrous ion is preferbly supplied by transferrin at from about 0.05 to about 50 ug/ml, i.e., about $5.6\times10^{-5}$ to about $5.6\times10^{-2}M$.

It is expected that the systems, methods and media of the present invention may be useful in the culture of a variety of cell types. Cells which are preferably cultured by the practice of the present invention are epithelial cells. Preferred epithelial cells include epidermal cells or keratinocytes.

Cell culture systems of the present invention comprise a cell culture medium as described above and a substrate for the cells comprising plastic, glass, collagen, fibronectin, laminin, heparan sulfate proteoglycan, microcarriers coated with collagen, fibronectin, laminin or heparan sulfate proteoglycan, or a tissue equivalent produced by a method comprising:

a. combining a collagen solution with a contractile agent under conditions to form a gel mixture having the contractile agent dispersed within the gel mixture; and
b. maintaining the gel mixture prepared in step (a) under conditions which permit contraction of the gel mixture to form a tissue-equivalent.

A preferred type of collagen is native Type I collagen derived from bovine tendon.

One method of culturing epithelial cells in accordance with the present invention comprises, inoculating a growth substrate as described above with epithelial cells, and maintaining the cell culture system under conditions to promote cell growth. Cell growth achieved in such methods is characterized by a population doubling time of from about 16 to about 33 hours. Furthermore, cells may be serially cultured to achieve from about 20 to about 50 population doublings. In yet another embodiment of the present invention, the method further comprises adding calcium at a concentration greater than about 1.0 mM to enable stratification and differentiation of the cells while maintaining a colony forming efficiency of from about 20 to about 60%. This is important in formation of living skin equivalents and sheets of epidermis for grafting. The practice of the present invention also provides for clonal growth of cells, i.e., seeding at a cell density of from about 30 to about 1000 cells.

By the practice of the present invention, it is possible to achieve rapid expansion of primary cells with a colony forming efficiency of from about 20 to about 100%, and a proliferative capacity in excess of 50 population doublings. Furthermore, calcium can be added in excess of 1.0 mM to enable stratification and differentiation of the cells while maintaining a colony forming efficiency of from about 20 to about 60%.

The present invention also provides a method of culturing epithelial cells on microcarriers, the method comprising plating epithelial cells onto collagen-coated microcarriers in a cell culture system as described above at a plating efficiency of from about 20 to about 40%, and maintaining the microcarriers and plated cells under conditions to promote cell growth. By the practice of this method, a colony forming efficiency of from about 20 to about 100% is maintained even as cell growth reaches confluence. Furthermore, calcium concentration may be increased from 0.08 to about 1.8 mM during the rapid proliferative phase when cell growth is approaching confluence to increase adherence of the cells to microcarriers and, thus, reduce cell loss through the shearing forces exerted on the microcarriers.

Fully epidermalized living tissue equivalents may also be made in accordance with the present invention. The method comprises the steps of:

a. innoculating a tissue equivalent in accordance with claim 14 with epidermal cells;
b. maintaining the cell culture system under conditions to promote cell growth; and
c. adding calcium to a physiological concentration and maintaining the system under conditions to enable development of a fully keratinized epidermal layer.

Media in accordance with the present invention will be conditioned by rapidly proliferating epithelial cells and it is expected that such conditioned media will be useful as growth supplements and in therapeutic applications such as wound healing.

DETAILED DESCRIPTION OF THE INVENTION

Chemically defined media in accordance with the present invention provide for culture of cells in the absence of feeder cells, serum or other components which may contribute undefined proteins to the media.

Some of the advantages of the media of the present invention are: ease of fabrication, flexibility of use, i.e, it can be used with varied calcium concentration, varied serum concentrations, varied growth factor additions and varied extracellular matrix components. The media and systems of the present invention provide the cell biologist and others interested in the fabrication and/or study of epithelium in vitro with a system to meet most of their needs.

One medium in accordance with the present invention comprises: insulin or an insulin-like growth factor; transferrin or ferrous ion; triiodothyronine or thyroxin; ethanolamine and/or o-phosphoryl-ethanolamine; calcium; and a nutrient source. Other components may be added to the media, depending upon, e.g., the particular cell being cultured, including but not limited to, epidermal growth factor (EGF), hydrocortisone, strontium, Bovine Hypothalamic Extract, progesterone, selenium and cAMP elevating agents. Hydrocortisone is reported to have value in the long term culture of normal human keratinocytes (Rheinwald and Green, supra) and is, therefore, a preferred component of complete mSBM. When minimal supplementation is desired, however, hydrocortisone is not required, and its absence may then be preferred.

Insulin is present at a concentration of from about 0.05 to about 500 ug/ml, a preferred range being from about 0.5 to about 50 ug/ml, and a particularly preferred concentration being 5.0 ug/ml. Proinsulin, IGF-1 ($10^{-10}$ to $10^{-8}$M) or other insulin-like growth factors may be substituted for insulin, although insulin is presently preferred for reasons of economy. Insulin-like growth factor as used herein means compositions which are structurally similar to insulin and stimulate the insulin-like growth factor receptors, e.g., Insulin-like Growth Factors I and II.

Ferrous ion may be provided by a ferrous salt such as ferrous sulfate at a concentration of from about $5 \times 10^{-8}$ to about $5 \times 10^{5}$M, preferably at about $5 \times 10^{-6}$M. More preferably, ferrous is supplied by transferrin at a concentration of from about 0.05 to about 50 ug/ml, a preferred concentration being about 5 ug/ml.

Triiodothyronine is preferred over thyroxin because it has been found to have a more potent effect in the claimed cell culture systems. Triiodothyronine is preferably present at a concentration of from about 2 to about 200 pM, more preferably at about 20 pM.

Ethanolamine and/or o-phosphoryl-ethanolamine may be used in the practice of the present invention. However, it is preferred to use these components in combination. Ethanolamine is present at a concentration of from about $10^{-6}$ to about $10^{-2}$M, more preferably about $10^{-4}$M. o-phosphoryl-ethanolamine is present at a concentration of from about $10^{-6}$ to about $10^{-2}$M, more preferably $10^{-4}$M.

In contrast with presently available media, the calcium concentration can be varied over a wide range in the media of the present invention while still maintaining an actively proliferating cell culture. Although cells may be grown in the media of the present invention at serum concentrations of 5% and at physiological calcium levels of 1.8 mM, growth and lack of terminal differentiation (i.e., maintenance of the proliferating basaloid cell population) are optimized by reducing the serum to about 0.3% or less, preferably 0%, and having a calcium concentration at from about 0.005 to about 2.0 mM, more preferably from about 0.08 to about 1.0 mM.

Under calcium conditions used for optimal growth rate, minimal stratification is seen. If these cultures are held at confluence, larger cells are released from the dish and the dish remains populated by a tightly packed layer of small cells. Addition of calcium allows stratification of the more mature cells while still maintaining a confluent basal cell layer. If calcium is added before confluence to 1.8 mM the appearance of the colonies and cell distribution parallels what was observed with feeder cells with the cells continuing to grow to confluence. There is little involucrin or transglutaminase (markers of epidermal cell differentiation) before confluence, if the calcium is kept at 1.0 mM or lower. Calcium is present at from about 0.005 to about 2.0 mM depending upon the purposes for culturing the cells. In some instances, rather than being added separately, the calcium needed is provided by other components in the medium.

Epidermal Growth Factor (EGF) is present at from about 1 to about 50 ng/ml, preferably at about 10 ng/ml (mouse EGF), and at about 1 ng/ml (human EGF). Although EGF is preferred, transforming growth factor-alpha, human or mouse, may be substituted for EGF, preferably at about 10 ng/ml (mouse) and about 1 ng/ml (human). Although EGF is an optional ingredient in media in accordance with the present invention, it may be preferred for some applications, e.g., large scale batch cultures.

Hydrocortisone is preferably at a concentration of from about 0.04 to about 4.0 ug/ml, a particularly preferred concentration being 0.4 ug/ml.

In yet other embodiments of the present invention, the medium of the present invention may be supplemented with additional components.

In some instances, it may be desirable to include components which inhibit fibroblast growth, such as cholera toxin.

Bovine hypothalmic extract (BHE) at from about 5 to about 200 ug/ml, preferably about 50 ug/ml, may be included to increase plating efficiency and colony formation in primary and in clonal density culture, particularly when initial cell density is less than about $1 \times 10^3$ cells/cm$^2$. Members of the fibroblast growth factor family, including acidic FGF, keratinocyte growth factor, and basic FGF (at a slightly higher concentration) may be substituted for BHE with similar effects at from about $10^{-10}$ g/ml to about $10^{-6}$ g/ml, preferably about $10^{-7}$ g/ml. Typically, BHE provides little or no advantage when cells are plated at $1 \times 10^3$ cells/cm$^2$ or higher. Other components which may be added to the medium described above include adenine from about 0.02 mM to about 2.0 mM; chelexed serum from 0% to about 2.00%; progesterone from about $2 \times 10^{-10}$ to about $2 \times 10^{-8}$M, preferably $2 \times 10^{-9}$M; selenium from about $1 \times 10^{-9}$ to about $1 \times 10^{-7}$M. Progesterone, selenium, BHE may be added in some instances to achieve optimal growth.

Cyclic AMP elevating agents, serum and bovine hypothalamic extract are not necessary to establish primary cell cultures and to pass human epidermal cells in the systems of the present invention. Previous investigators have shown both the addition of cAMP elevating agents and the presence of bovine pituitary extract to be beneficial, if not essential, for establishing primary cultures of epidermal cells (See Green, 1978, supra., and Boyce and Ham, 1985, supra). Although the addition of BHE may be slightly beneficial, the data in Example 9, below, show that neither BHE nor cAMP elevating agents are necessary for primary culture and subsequent passage of epidermal cells using the media of the present invention. However, cAMP elevating agents may be used in the practice of the present invention if desired.

Cyclic AMP elevating agents which may be used in the practice of the present invention include cholera toxin, foreskolin, β-adrenergic agents such as adrenalin, theophylline, dibutyryl cyclic AMP, methyl isobutyl xanthine, isoproterenol, caffeine and pertussis toxin. Preferred agents include cholera toxin and foreskolin. Cholera toxin is preferably used at from about $10^{-8}$ to about $10^{-5}$M; and foreskolin from about $10^{-9}$ to about $10^{-3}$M, preferably from about $10^{-7}$ to about $10^{-5}$M, and more preferably at $10^{-6}$M.

The use of c-AMP elevating agents in the systems and media of the present invention may be benefical in some cases when establishing primary cultures or in reestablishing primary cultures or other cells which have been frozen. However, in the practice of the present invention cells can be readily established without the addition of a cAMP elevating agent or BHE. Such cells can subsequently be passed for multiple passages using the media of the current invention without a cAMP elevating agent.

The addition of cation substitutes was investigated as possible replacement for the constitutive need for calcium. While all cells require a certain level of calcium, calcium also has differentiation promoting effects in keratinocytes. It had been previously shown that other divalent cations could replace the cells' consituitive need (Rubin, *J. Cell. Physiol.*, 91 (1977) 449–458) without contributing to induction of differentiation (Praeger et al. *J. Cell. Physiol.*, 132 (1987) 81–89, Furakawa et al., *J. Invest. Dermatol.*, 90 (1988) 690–696). The effects of strontium and magnesium were investigated in the systems of the present invention. Magnesium was found in some instances to have a beneficial effect. Strontium addition, while not significantly changing the proportion of proliferative cell population (9–14 um distribution), significantly increased the final cell yield and reduced the population doubling time by approximately 4 hours. See Example 8, below.

Nutrient sources useful in the practice of the present invention provide known essential nutrients for cultured cells, such as: an energy source such as glucose, fructose or galactose; both essential and nonessential amino acids; both water-soluble (B group, biotin, folic acid, nicotinamide, panthothenic acid, pyroxidine, riboflavin and thiamine) and fat-soluble (A, D, E, K, and ubiquinone) vitamins; major inorganic ions such as bicarbonate, calcium, chloride, magnesium, phosphate, potassium and sodium; trace elements such as As, Co, Gr, Cu, F, Fe, Mn, Mo, Ni, Se, Si, Sn, V and Zn; lipids; buffers, e.g., like CO2/HCO3 and HEPES; gases (oxygen and carbon dioxide); and nucleic acid precursors like adenine, cytidine, hypoxanthine, and thymidine.

There are many commercially available nutrient sources which are expected to be useful in the practice of the present invention. These include commerically available nutrient sources which supply inorganic salts, an energy source, amino acids, and B-vitamins, such as Dulbecco's Modified Eagle's Medium (DMEM); Minimum Essential Medium (MEM); M199; RPMI 1640; (all available from Flow Laboratories); and Iscove's Modified Dulbecco's Medium (EDMEM, Gibco Labs). Minimum Essential Medium and M199 require additional supplementation with phospholipid precursors and non-essential amino acids. Commercially available vitamin rich mixtures which supply additional amino acids, nucleic acids, enzyme cofactors, phospholipid precursors, and inorganic salts, include Ham's F12; Ham's F10; NCTC 109; (all available from Flow Laboratories) and NCTC 135 (Irvine Scientific).

The components of each of the above nutrient sources is provided hereinafter.

| | Dulbecco's Modified Eagle's Medium |
|---|---|
| COMPONENT | 1X MEM (Modified) Dulbecco's Modification Liquid without L-Glutamine Product No. 12-332 mg/L |
| INORGANIC SALTS | |
| $CaCl_2$ | |
| $CaCl_2 \cdot 2H_2O$ | 264.90 |
| $Fe(NO_3)_3 \cdot 9H_2O$ | 0.10 |
| KCl | 400.0 |
| $MgSO_4$ | |
| $MgSO_4 \cdot 7H_2O$ | 200.00 |
| NaCl | 6400.00 |
| $NaHCO_3$ | 3700.00 |
| $NaH_2PO_4 \cdot H_2O$ | 125.00 |
| OTHER COMPONENTS | |
| Fructose | |
| Glucose | 4500.0 |
| Lipoic Acid | |
| Phenol Red, Na | 15.0 |
| Sodium Pyruvate | 110.0 |
| Aminopterin | |
| Hypoxanthine | |
| Thymidine | |
| AMINO ACIDS | |
| L-arginine.HCl | 84.00 |
| L-cystine | 48.00 |
| L-cystine, $Na_2$ | |
| L-glutamine | |
| Glycine | 30.00 |
| L-histidine.HCl.$H_2O$ | 42.00 |
| L-isoleucine | 104.80 |
| L-leucine | 104.80 |
| L-lysine.HCl | 146.20 |
| L-methionine | 30.00 |
| L-phenylalanine | 66.00 |
| L-serine | 42.00 |
| L-threonine | 95.20 |
| L-tryptophan | 16.00 |
| L-tyrosine | 72.00 |
| L-valine | 93.60 |
| VITAMINS | |
| D-Ca Pantothenate | 4.00 |
| Choline Chloride | 4.00 |
| Folic Acid | 4.00 |
| i-Inositol | 7.00 |
| Nicotinamide | 4.00 |
| Pyridoxal.HCl | 4.00 |
| Riboflavin | 0.40 |
| Thiamin.HCl | 4.00 |

| | Minimal Essential Medium with Hank's Salts or Earl's Salts | |
|---|---|---|
| COMPONENT | 1X MEM (Modified) Earle's Salts Liquid without L Glutamine Product No. 12-102 mg/L | 1X MEM (Modified) Hank's Salts Liquid without L Glutamine Product No. 12-132 mg/L |
| INORGANIC SALTS | | |
| $CaCl_2$ | | |
| $CaCl_2 \cdot 2H_2O$ | 264.9 | 185.5 |
| KCl | 400.0 | 400.0 |
| $KH_3PO_4$ | | 60.0 |
| $MgSO_4$ | | |
| $MgSO_4 \cdot 7H_2O$ | 200.0 | 200.0 |
| NaCl | 6800.0 | 8000.0 |

-continued

| Component | | |
|---|---|---|
| NaHCO₃ | 2000.0 | 350.0 |
| NaH₂PO₄.H₂O | 140.0 | |
| Na₂HPO₄ | | 47.5 |
| Hepes | | |
| OTHER COMPONENTS | | |
| Glucose | 1000.0 | 1000.0 |
| Phenol Red, Na | 17.0 | 17.0 |
| Sodium Succinate.6H₂O | | |
| Succinic Acid | | |
| AMINO ACIDS | | |
| L-alanine | | |
| L-arginine.HCl | 126.40 | 126.40 |
| L-asparagine.H₂O | | |
| L-aspartic Acid | | |
| L-cystine | 24.02 | 24.02 |
| L-cystine, Na₂ | | |
| L-glutamic Acid | | |
| L-glutamine | | |
| Glycine | | |
| L-histidine.HCl.H₂O | 41.90 | 41.90 |
| L-isoleucine | 52.50 | 52.50 |
| L-leucine | 52.50 | 52.50 |
| L-lysine.HCl | 73.06 | 73.06 |
| L-methionine | 14.90 | 14.90 |
| L-phenylalanine | 33.02 | 33.02 |
| L-proline | | |
| L-serine | | |
| L-threonine | 47.64 | 47.64 |
| L-tryptophan | 10.20 | 10.20 |
| L-tryosine | 36.22 | 36.22 |
| L-valine | 46.90 | 46.90 |
| VITAMINS | | |
| D-Ca Pantothenate | 1.00 | 1.00 |
| Choline Bitartrate | | |
| Choline Chloride | 1.00 | 1.00 |
| Folic Acid | 1.00 | 1.00 |
| I-Inositol | 2.00 | 2.00 |
| Nicotinamide | 1.00 | 1.00 |
| Pyridoxal.HCl | 1.00 | 1.00 |
| Riboflavin | 0.10 | 0.10 |
| Thiamin.HCl | 1.00 | 1.00 |

RPMI 1640 Medium

| COMPONENT | 1X RPMI 1640 Liquid without L-Glutamine Product No. 12-602 mg/L |
|---|---|
| INORGANIC SALTS | |
| Ca(NO₃)₃.4H₂O | 100.0 |
| KCl | 400.0 |
| MgSO₄ | |
| MgSO₄.7H₂O | 100.0 |
| NaCl | 6000.0 |
| NaHCO₃ | 2000.0 |
| Na₂HPO₄ | 800.7 |
| HEPES | |
| OTHER COMPONENTS | |
| Glucose | 2000.0 |
| Glutathione | 1.00 |
| Phenol Red, Na | 5.0 |
| Hypoxanthine | |
| Aminopterin | |
| Thymidine | |
| AMINO ACIDS | |
| L-arginine | 200.00 |
| L-asparagine.H₂O | 56.82 |
| L-aspartic Acid | 20.00 |
| L-cystine | 50.00 |
| L-cystine, Na₃ | |
| L-glutamic Acid | 20.00 |
| L-glutamine | |
| Glycine | 10.00 |
| L-histidine | 15.00 |
| L-hydroxyproline | 20.00 |
| L-isoleucine | 50.00 |
| L-leucine | 50.00 |
| L-lysine.HCl | 40.00 |
| L-methionine | 15.00 |
| L-phenylalanine | 15.00 |
| L-proline | 20.00 |
| L-serine | 30.00 |
| L-threonine | 20.00 |
| L-tryptophan | 5.00 |
| L-tyrosine | 20.00 |
| L-valine | 20.00 |
| VITAMINS | |
| Biotin | 0.20 |
| D-Ca Pantothenate | 0.25 |
| Choline Chloride | 3.00 |
| Folic Acid | 1.00 |
| I-Inositol | 35.00 |
| Nicotinamide | 1.00 |
| PABA | 1.00 |
| Pyroxidine.HCl | 1.00 |
| Riboflavin | 0.20 |
| Thiamin.HCl | 1.00 |
| Vitamin B₁₂ | 0.005 |

REFERENCES:
1 Moore, G. E., et al. 1967, JAMA, 199 519
2 Morton, J. H., 1970, In Vitro, 6 89

Medium 199
(Modified)

| COMPONENT | 1X Medium 199 (Modified) with Earle & Salts Liquid with L-Glutamine Product No. 12-203 mg/L |
|---|---|
| INORGANIC SALTS | |
| CaCl₂ | |
| CaCl₂.2H₂O | 264.9 |
| Fe(NO₁)₃.9H₂O | 0.10 |
| KCl | 400.0 |
| KH₃PO₃ | |
| MgSO₄ | |
| MgSO₃.7H₂O | 200.0 |
| NaCl | 6800.0 |
| NaHCO₂ | 2200.0 |
| NaH₃PO₄.H₂O | 140.0 |
| Na₃HPO₂ | |
| OTHER COMPONENTS | |
| Adenine-SO₄ | 10.00 |
| S-Adenylic Acid | 0.20 |
| ATP,Na₃ | 10.00 |
| DL-tocopherol-PO₄, Na₂ | 0.01 |
| Cholesterol | 0.20 |
| 2-Deoxy-D-Ribose | 0.50 |
| Glucose | 1000.00 |
| Glutathione | 0.05 |
| Guanine.HCl | 0.30 |
| Hypoxanthine | 0.30 |
| Phenol Red, Na | 17.0 |
| D-ribose | 0.50 |
| Sodium Acetate | 36.71 |
| Thymine | 0.30 |
| Tween 80 | 5.00 |
| Urecil | 0.30 |
| Xanthine | 0.30 |
| AMINO ACIDS | |
| L-alanine | 25.00 |
| L-arginine.HCl | 70.00 |
| L-aspartic Acid | 30.00 |

-continued

| Component | |
|---|---|
| L-cysteine.HCl.H₂O | 0.11 |
| L-cystine | 20.00 |
| L-cystine, Na₂ | |
| L-glutamic Acid | 66.82 |
| L-glutamine | 100.00 |
| Glycine | 50.00 |
| L-histidine.HCl.H₂O | 21.88 |
| L-hydroxyproline | 10.00 |
| L-isoleucine | 20.00 |
| L-leucine | 60.00 |
| L-lysine.HCl | 70.00 |
| L-methionine | 15.00 |
| L-phenylalanine | 25.00 |
| L-proline | 40.00 |
| L-serine | 25.00 |
| L-threonine | 30.00 |
| L-tryptophan | 10.00 |
| L-tryosine | 40.00 |
| L-valine | 25.00 |
| VITAMINS | |
| L-ascorbic Acid | 0.050 |
| Biotin | 0.010 |
| Calciterol | 0.100 |
| D-Ca Paniothenate | 0.010 |
| Choline Chloride | 0.500 |
| Folic Acid | 0.010 |
| I-Inositol | 0.050 |
| Menadione | 0.010 |
| Menadione Na Bisulfile.3H₂O | |
| Niacin | 0.025 |
| Nicotinamide | 0.025 |
| PABA | 0.050 |
| Pyridoxal.HCl | 0.025 |
| Pyridoxine.HCl | 0.025 |
| Riboflavin | 0.010 |
| Thiamin.HCl | 0.010 |
| Vitamin A Acetate | 0.047 |

Ham's F-10 Medium

| COMPONENT | 1X Ham's F10. Liquid with L-Glutamine Product No. 12-403 mg/L |
|---|---|
| INORGANIC SALTS | |
| CaCl₂ | |
| CaCl₂.2H₂O | 44.1 |
| CuSO₄ | 0.0016 |
| FeSO₄ | 0.456 |
| KCl | 285.0 |
| KH₂PO₄ | 83.0 |
| MgSO₄ | |
| MgSO₄.7H₂O | 152.7 |
| NaCl | 7400.0 |
| NaHCO₃ | 1200.0 |
| Na₂HPO₄ | 156.2 |
| ZnSO₄.7H₂O | 0.0288 |
| OTHER COMPONENTS | |
| Glucose | 1100.0 |
| Hypoxanthine | 4.08 |
| Lipoic Acid | 0.206 |
| Methyl Linoleate | |
| Phenol Red, Na | 1.24 |
| Putrescine.2 HCl | |
| Sodium Pyruvate | 110.0 |
| Thymidine | 0.727 |
| AMINO ACIDS | |
| L-alanine | 8.91 |
| L-arginine.HCl | 210.70 |
| L-asparagine.H₂O | 15.01 |
| L-aspartic Acid | 13.31 |
| L cysteine.HCl.H₂O | 35.13 |
| L-glutamic Acid | 14.71 |
| L-glutamine | 146.20 |
| Glycine | 7.51 |
| L-histidine.HCl.H₂O | 20.96 |
| L-isoleucine | 2.62 |
| L-leucine | 13.12 |
| L-lysine.HCl | 29.30 |
| L-methionine | 4.48 |
| L-phenylalanine | 4.96 |
| L-proline | 11.51 |
| L-serine | 10.51 |
| L-threonine | 3.57 |
| L-tryptophan | 0.61 |
| L-tyrosine | 1.81 |
| L-valine | 3.51 |
| VITAMINS | |
| Biotin | 0.024 |
| D-Ca Paniothenate | 0.715 |
| Choline Chloride | 0.698 |
| Folic Acid | 1.32 |
| I-Inositol | 0.541 |
| Nicotinamide | 0.611 |
| Pyridoxine.HCl | 0.206 |
| Riboflavin | 0.376 |
| Thiamin.HCl | 1.012 |
| Vitamin B₁₂ | 1.36 |

Ham's F-12 Medium

| COMPONENT | 1X Ham's F12 Liquid with L-Glutamine Product No. 12-423 mg/L |
|---|---|
| INORGANIC SALTS | |
| CaCl₂ | |
| CaCl₂.2H₂O | 44.1 |
| CuSO₄ | 0.0016 |
| FeSO₄ | 0.456 |
| KCl | 223.7 |
| KH₂PO₄ | |
| MgSO₄ | |
| MgSO₄.7H₂O | 147.9 |
| NaCl | 7600.0 |
| NaHCO₃ | 1176.0 |
| Na₂HPO₄ | 142.0 |
| ZnSO₄.7H₂O | 0.863 |
| OTHER COMPONENTS | |
| Glucose | 1802.0 |
| Hypoxanthine | 4.08 |
| Lipoic Acid | 0.206 |
| Methyl Linoleate | 0.088 |
| Phenol Red, Na | 1.24 |
| Putrescine.2 HCl | 0.1611 |
| Sodium Pyruvate | 110.0 |
| Thymidine | 0.727 |
| AMINO ACIDS | |
| L-alanine | 8.91 |
| L-arginine.HCl | 210.70 |
| L-asparagine.H₂O | 15.01 |
| L-aspartic Acid | 13.31 |
| L cysteine.HCl.H₂O | 35.13 |
| L-glutamic Acid | 14.71 |
| L-glutamine | 146.20 |
| Glycine | 7.51 |
| L-histidine.HCl.H₂O | 20.96 |
| L-isoleucine | 3.94 |
| L-leucine | 13.12 |
| L-lysine.HCl | 36.53 |
| L-methionine | 4.48 |
| L-phenylalanine | 4.96 |
| L-proline | 34.54 |
| L-serine | 10.51 |
| L-threonine | 11.91 |
| L-tryptophan | 2.04 |
| L-tyrosine | 5.44 |
| L-valine | 11.72 |

VITAMINS

| | |
|---|---|
| Biotin | 0.0073 |
| D-Ca Paniothenate | 0.238 |
| Choline Chloride | 13.96 |
| Folic Acid | 1.32 |
| I-Inositol | 18.02 |
| Nicotinamide | 0.037 |
| Pyridoxine.HCl | 0.062 |
| Riboflavin | 0.038 |
| Thiamin.HCl | 0.337 |
| Vitamin $B_{12}$ | 1.36 |

NCTC MEDIUM 109 AND 135

1. Evans, V. J.: Bryant, J. C.: Kerr, H. A. & Schilling, E. L., Exp. Cell Res. 36:439–474, 1964
2. Morton, H., In Vitro 6:89–108, 1970

| COMPONENT | mg/L |
|---|---|
| L-Alanine | 31.48 |
| L-Amino-n-butyric Acid | 5.51 |
| L-Arginine HCl | 31.16 |
| L-Asparagine-$H_2O$ | 9.19 |
| L-Aspartic Acid | 9.91 |
| L-Cystine.2HCl | 13.67$^A$ |
| *L-Cysteine HCl.$H_2O$* | 289.71$^A$ |
| D-(+)Glucosamine.HCl | 3.85 |
| L-Glutamic Acid | 8.26 |
| *L-Glutamine | 135.73 |
| Glycine | 13.51 |
| L-Histidine HCl.$H_2O$ | 26.65 |
| L-Hydroxyproline | 4.09 |
| L-Isoleucine | 18.04 |
| L-Leucine | 20.44 |
| L-Lysine HCl | 38.43 |
| L-Methionine | 4.44 |
| L-Ornithine HCl | 9.41 |
| L-Phenylalanine | 16.53 |
| L-Proline | 6.13 |
| L-Serine | 10.75 |
| L-Taurine | 4.18 |
| L-Threonine | 18.93 |
| L-Tryptophan | 17.50 |
| L-Tyrosine, 2Na.$2H_2O$ | 23.70$^A$ |
| L-Valine | 25.00 |
| p-Aminobenzoic Acid | 0.125 |
| *Ascorbic Acid | 50.0 |
| d-Biotin | 0.025 |
| Calciferol (Vitamin $D_2$) | 0.25 |
| D-Ca Pantothenate | 0.025 |
| Choline Chloride | 1.25 |
| Folic Acid | 0.025 |
| i-Inositol | 0.125 |
| Menadione (Vitamin $K_3$) | 0.025 |
| Niacin (Nicotinic Acid) | 0.0625 |
| Niacinamide (Nicotinamide) | 0.0625 |
| Pyridoxal HCl | 0.0625 |
| Pyridoxine HCl | 0.0625 |
| Riboflavin | 0.025 |
| Thiamine HCl | 0.025 |
| α-Tocopherol Phosphate, 2Na | 0.025 |
| *Vitamin A | 0.25 |
| Vitamin $B_{12}$ | 10.0 |
| D-Glucuronolactone | 1.80 |
| Glutathione, Monosodium | 10.0 |
| Sodium Glucuronate.$H_2O$ | 1.80 |
| *Tween 80$^2$ | 12.50 |
| *Ethyl Alcohol | 40.0$^B$ |
| *CO A (Coenzyme A) | 2.50 |
| *DPN (Diphosphopyridine nucleotide) | 7.00 |
| *FAD (Flavin-adenine dinucleotide) | 1.00 |
| *TPN (Triphosphopyridine Nucleotide, Na) (NADP) | 1.00 |
| *TPP (Cocarboxylase) | 1.00 |

NCTC MEDIUM 109 AND 135

1. Evans, V. J.: Bryant, J. C.: Kerr, H. A. & Schilling, E. L., Exp. Cell Res. 36:439–474, 1964
2. Morton, H., In Vitro 6:89–108, 1970

| COMPONENT | mg/L |
|---|---|
| *UTP (Uridine triphosphate, Na) | 1.00 |
| Deoxyadenosine | 10.00 |
| Deoxycytidine.HCl | 10.00 |
| Deoxyguanosine | 10.00 |
| *5-Methylcytosine | 0.10 |
| Thymidine | 10.0 |
| $CaCl_2$ | 200.0 |
| KCl | 400.0 |
| $MgSO_4$ (anhyd) | 100.0 |
| NaCl | 6800. |
| $NaH_2PO_4.H_2O$ | 140.0 |
| D-Glucose | 1000. |
| Phenol Red, Na Salt | 20.0$^C$ |
| Sodium Acetate.$3H_2O$ | 50.0 |
| $NaHCO_3$ | 2200 |

*NCTC 109 AND 135 list the same components (reference 2) except that NCTC 135 omits L-Cysteine HCl. Reference 1, page 466, notes toxicity of Cysteine as one reason for omitting it from the 135 formulation.
*NCTC 109/135 BASE media (9172 & 9502) omit the marked (*) components. See Media introduction for additional information about base media.
$^A$Reference 2 lists L-Cystine 10.49 mg/L. L-Cysteine HCl 250 mg/L. L-Tyrosine 16.44 mg/L.
$^B$Omitted from powdered media
$^C$PLAQUE ASSAY (2X) Media omit phenol red and glutamine and double amounts of all other components
*Trademark of ICI America's, Inc

ISCOVE'S MODIFIED DULBECCO'S MEDIUM

| COMPONENT | Liquid (1X) Form.No.78-0415 mg/L | Powder Cat.No.430-2200 mg/L |
|---|---|---|
| INORGANIC SALTS: | | |
| $CaCl_2$ (anhyd.) | 165.00 | 165.00 |
| $Fe(NO_3)_3.9H_2O$ | — | — |
| KCl | 330.00 | 330.00 |
| $KNO_3$ | 0.076 | 0.076 |
| $MgSO_4$ (anhyd.) | 97.67 | 97.67 |
| $MgSO_4.7H_2O$ | — | — |
| NaCl | 4505.00 | 4505.00 |
| $NaHCO_3$ | 3024.00 | — |
| $NaH_2PO_4.H_2O$ | 125.00 | 125.00 |
| $Na_2SeO_3.5H_2O$ | 0.0173 | 0.0173 |
| OTHER COMPONENTS: | | |
| D-Glucose | 4500.00 | 4500.00 |
| Phenol red | 15.00 | 15.00 |
| HEPES | 5958.00 | 5958.00 |
| Sodium pyruvate | 110.00 | 110.00 |
| AMINO ACIDS: | | |
| L-Alanine | 25.00 | 25.00 |
| L-Asparagine.$H_2O$ | 28.40 | 28.40 |
| L-Arginine.HCl | 84.00 | 84.00 |
| L-Aspartic acid | 30.00 | 30.00 |
| L-Cystine | — | — |
| L-Cystine.2HCl | 91.24 | 91.24 |
| L-Glutamic acid | 75.00 | 75.00 |
| L-Glutamine | 584.00 | 584.00 |
| Glycine | 30.00 | 30.00 |
| L-Histidine HCl.$H_2O$ | 42.00 | 42.00 |
| L-Isoleucine | 105.00 | 105.00 |
| L-Leucine | 105.00 | 105.00 |
| L-Lysine HCl | 146.00 | 146.00 |
| L-Methionine | 30.00 | 30.00 |
| L-Phenylalanine | 66.00 | 66.00 |
| L-Proline | 40.00 | 40.00 |
| L-Serine | 42.00 | 42.00 |

-continued

ISCOVE'S MODIFIED DULBECCO'S MEDIUM

| COMPONENT | Liquid (1X) Form.No.78-0415 mg/L | Powder Cat.No.430-2200 mg/L |
|---|---|---|
| L-Threonine | 95.00 | 95.00 |
| L-Tryptophane | 16.00 | 16.00 |
| L-Tyrosine | — | — |
| L-Tyrosine (Disodium salt) | 104.20 | 103.79 |
| L-Valine | 94.00 | 94.00 |
| VITAMINS: | | |
| Biotin | 0.013 | 0.013 |
| D-Ca pantothenate | 4.00 | 4.00 |
| Choline chloride | 4.00 | 4.00 |
| Folic acid | 4.00 | 4.00 |
| i-Inositol | 7.20 | 7.20 |
| Nicotinamide | 4.00 | 4.00 |
| Pyridoxal HCl | 4.00 | 4.00 |
| Riboflavin | 0.40 | 0.40 |
| Thiamine HCl | 4.00 | 4.00 |
| Vitamin $B_{12}$ | 0.013 | 0.013 |

It should be understood that each of the above nutrient sources are available with slight component variations, some of which will be acceptable nutrient sources for use in the present invention.

A preferred nutrient source for use in the present invention comprises $Ca^{++}$ Free DMEM from about 90 to about 10% and Ham's F 12 from about 10% to about 90%. A particularly preferred source comprises $Ca^{++}$ Free DMEM at about 75% and Ham's F 12 at about 25%. Typically, the media of the present invention comprises at least about 90% and preferably greater than nutrient source.

One preferred medium of the present invention comprises:

| | |
|---|---|
| Insulin: | 5 ug/ml; |
| Transferrin: | 5 ug/ml; |
| Triiodothyronine: | 20 pM; |
| Ethanolamine: | $1 \times 10^{-4}$ M; |
| o-phosphoryl-ethanolamine: | $1 \times 10^{-4}$ M; |
| Adenine | 0.18 mM; |
| Selenium | $3 \times 10^{-8}$ M; |
| Strontium | 1 mM |
| Calcium: | 0.08 mM; and |
| Nutrient source: | $Ca^{++}$ Free DMEM from about 90 to about 10% and Ham's F 12 from about 10% to about 90%; |

If desired, hydrocortisone may be added at about 1.1 mM, EGF at 10 ng/ml; progesterone at $2 \times 10^{-9}$M and either BHE at about 50 ug/ml or cholera toxin at about 9 ng/ml may be added to further enhance growth rate or prolong life span. The pH of the medium is typically around neutrality, e.g., about pH 6.8–7.4.

A significant measure of the effectiveness of a culture medium is the growth rate of a cell type as given by population doublings per day. By use of the culture systems of the present invention, epithelial cells may be cultured in the absence of feeder cells and serum at low density to allow for expansion of primary culture in excess of 50 population doublings at a growth rate comparable to that in a feeder cell system. For example, keratinocytes from newborn foreskins rarely drop below 0.5 doublings per day in the media and systems of the present invention, averaging one doubling per day through passage 6, and can reach growth rates of 1.3 to 2.0 doublings per day between passages 2 and 5 (See Table 2, below). Growth rates of such magnitude indicate a population doubling in number every 12–18 hours.

By use of the systems and media of the present invention, calcium can be added to physiological concentration with maintenance of the basal cell layer, a result achieved hereto only with 3T3 systems. Thus, the culture systems and media of the present invention allow for the addition of calcium in excess of 1.0 mM without loss of a proliferative cell population, and, therefore, allow use of such cells in fabrication of living skin equivalents or in the formation of continuous sheets of epidermal cells suitable for grafting (See Example 6 below). Furthermore, the ability to vary calcium concentration without detrimental effects on cell growth now makes it possible to grow epidermal cells in large scale mirocarrier culture (See Example 7 below). For example, in MCDB 153 the calcium level has to be low in order to get cell growth but when the calcium level is low cells do not adhere well to the surface of the microcarrier, a disadvantage when the microcarrier is subjected to shear force. In the Rheinwald and Green 3T3 systems, supra, the microcarrier would first have to be coated with the 3T3 cells and the epithelial cells then grown on the 3T3 cells.

The media of the present invention are currently prepared from components which are readily available commercially, including the nutrient source which may conveniently be obtained commercially calcium free. Furthermore, the components of the subject media are prepared and assembled using techniques available to the skilled artisan. In contrast, it is believed, based on culture studies with commercially available equivalents to MCDB 153, that limited success has been achieved in making these equivalents.

The systems of the present invention are not only comparable to, but in some respects clearly superior to the 3T3 system, one of the most successful systems heretofore known for the culture of epithelial cells. The present invention provides cell growth media which is chemically defined and does not depend on serum or feeder cells to provide acceptable growth and expansion of the cultured cells. The media and systems of the present invention enable establishment of primary cultures with from about 0.5 to about 2.0 population doublings (PDL) per 24 hour period.

A comparison of presently available media described above with the claimed media and systems is set forth below:

COMPARISON OF SYSTEMS

| | MCDB 153 (Boyce/Ham) | Eisenger | RHEIN-WALD GREEN | PRESENT INVENTION |
|---|---|---|---|---|
| Lack of feeder cells | yes | yes | no | yes |
| Lack of cAMP elevating agents | yes | yes | no | yes |
| ≧50 pdl | no | no | yes | yes |
| >25% plating eff. | yes | no | no | yes |
| >20% cfe | yes | no | no | yes |
| Clonal growth | yes | no | yes | yes |
| Little or no serum | yes | no | no | yes |
| Avg. pdt < 24 hr. | yes | no | yes | yes |
| Growth in >1.0 mM $Ca^{++}$ | no | yes | yes | yes | pdl = population doubling; cfe = colony forming efficiency; ECM = extracellular matrix; pdt = population doubling time.

Various substrates can be used in the practice of the present invention including collagen, fibronectin, laminin, heparan sulfate proteoglycan and tissue equivalents, as described in the Patents. Native Type I collagen from bovine tendon is a preferred collagen substrate. In the claimed systems, growth may be enhanced under certain conditions using either fibronectin or collagen coated substrate (See Example 3). It can be advantageous to use, e.g., collagen, in the establishment of primary cultures or when serum is included in the media, at greater than about 1% or to establish cells from frozen stocks. However, when the serum concentration is reduced to about 0.3% or less, the detrimental or differentiation promoting serum effects are lessened to the extent that a matrix component no longer provides such advantages. If a substrate is used, it must be of high quality because, it was found that poorly coated dishes with either partially degraded fibronectin or uneven collagen could also inhibit cell growth and spreading.

The presence of a substrate, e.g., a matrix component appears to allow the cells to establish colonies when conditions are less than optimal or more stringent, e.g., in the presence of serum factors, low cell density, in establishment of cells from tissue, or, possibly, in application where even greater longevity is required.

Thus, we have described and provided examples of novel media and systems for the growth of cells, such as epithelial cells. This invention will be further understood with reference to the following examples which are purely exemplary in nature and which are not meant to be utilized to limit the scope of the invention.

In the following examples the basic medium used, designated mSBM, consisted of the following components:

| | |
|---|---|
| Hydrocortisone | 1.1 uM |
| Insulin | 5 ug/ml |
| Transferrin | 5 ug/ml |
| Triiodothyronine | 20 pM |
| Ethanolamine | $1 \times 10^{-4}$ M |
| o-phosphorylethanolamine | $1 \times 10^{-4}$ M |
| Adenine | 0.18 mM |
| Progesterone | $2 \times 10^{-9}$ M |
| Selenium | $3 \times 10^{-8}$ M |
| Cholera Toxin | 9 ng/ml |
| Epidermal Growth Factor | 10 ng/ml |
| Calcium Free DMEM | 75% |
| Ham's F-12 | 25% |

Unless otherwise noted, mSBM also included chelexed Fetal Bovine Serum (cFBS) at 0.3%. Although cFBS is not a necessary component of the medium, it was used because it was traditionally used in the cholera toxin supplement to allow prolonged frozen storage without loss of activity of the cholera toxin.

Another medium, designated emSBM, also used in the following examples, consisted of the components listed above with concentrations changes and the additional component listed below:

| | |
|---|---|
| Triiodothyronine | Increased to $1.002 \times 10^{-8}$ M |
| Cholera Toxin | Increased to 100 ng/ml |
| Bovine Hypothalamic Extract (BHE) | 50 ug/ml |

In Example 8 below strontium (Sr) was added to medium in certain instances and in Example 9 below a cAMP elevating agent was not included in the medium in certain instances. Cells were grown in accordance with Example 10 without exogenous cAMP elevating agents, progesterone, serum or bovine hypothalmic extract. In Example 11 cells were grown without EGF and in Example 13 without hydrocortisone.

Although primary cultures where established in emSBM, none of a cAMP elevating agent, serum, progesterone, elevated triiodothyronine or BHE are required, although BHE in some circumstances provides superior growth.

The medium described above is typically prepared as set forth below. However, it should be understood that the components of the present invention may be prepared and assembled using conventional methodology compatible with their physical properties. Media in accordance with the present invention are sterile. Sterile components are bought or rendered sterile by conventional procedures after preparation. Proper sterile procedures were used throughout the following examples. Stock solutions of all components can be stored at −20° C., with the exception of nutrient source which can be stored at 4° C.

All stock solutions are prepared at a concentration 500× the final concentrations listed above. Hydrocortisone (Sigma) is dissolved in absolute ethanol and diluted in phosphate buffered saline (PBS). A stock solution of insulin, transferrin and triiodothyronine (all from Sigma) is prepared as follows: triiodothyronine is initally dissolved in absolute ethanol: 1N HCl at 2:1. Insulin is dissolved in dilute HCl (approximately 0.1N) and transferrin is dissolved in water. The three are then mixed and diluted in water to a 500× concentration. Ethanolamine and o-phosphorylethanolamine (both from Sigma) are dissolved in water to 500× concentration, filter sterilized. Progesterone (Sigma) is dissolved in absolute ethanol and diluted with water. Bovine serum albumin (BSA) may be added for prolonged storage to maintain the activity. Selenium (Sigma) is prepared as is ethanolamine. Cholera toxin is purchased sterile from Sigma and is dissolved in water. EGF is purchased sterile from Biomedical Technologies, Inc. and is dissolved in PBS. Adenine is difficult to dissolve but may be dissolved by any number of methods known to those skilled in the art. Sterile calcium free DMEM is ordered from J. R. Scientific or Hazelton. Ham's F-12 is ordered from M. A. Bioproducts. BHE (Collaborative Research, i.e., ECGS) is dissolved in low calcium DMEM. BSA may be added to prolong the storage life of the EGF stock solution. DMEM and F-12 are combined and the individual components are then added to complete the medium. The medium can be either used immediately after preparation or, stored at 4° C. If stored frozen, EGF should not be added until the time of use. The resulting media is sterile.

The activity of both BHE and EGF are evaluated on a lot by lot basis. Growth achieved in medium lacking BHE or EGF is compared with growth in medium containing these ingredients, from a range of concentrations from about 0 to about 50 ng/ml EGF and from about 0 to about 200 ug/ml BHE in order to determine the concentration which will support maxium growth.

EXAMPLE 1

Establishment of Primary Cultures

Foreskin and other tissue, including ear and abdomen, were obtained from routine biopsies and washed for 2 minutes in phosphate buffered saline (PBS) containing gentamicin at 50 mcg/ml and fungizone at 1.25 meq. Whole tissue samples were then washed for 1 min. in 95% ethanol to remove surface contamination, followed by washing again in the PBS-gentamicin fungizone solution. Subcutaneous tissue was removed aseptically and the tissue rinsed in the PBS-gentamicin fungizone solution and minced into approximately 1 mm² pieces. Minced tissue was dissociated at 37° C. using a collagenase-trypsin tissue mixture. The components of the collagenease dissociation mix used are as follows: collagenase 55.5 mg/ml; trypsin 2.0 mg/ml; glucose 0.375 mg/ml; fungizone 1 meq/ml; and gentamicin 50 mcg/ml in phosphate buffered saline. Digest supernatant was removed and neutralized and fresh enzyme added to the remaining digested pieces at 30 minute intervals until the tissue was fully dissociated.

Cell fractions containing a mixed population of dissociated cells were pooled, counted and plated at $2.6 \times 10^4/cm^2$ on T75 flasks (collagen coated at 5 ug/cm$^2$) with a total volume of 10 mls of emSBM which does not contain EGF. Primary cultures such as this became confluent in 7–17 days. One day post plating, emSBM was aspirated off and replaced with fresh emSBM containing 10 ng/ml EGF. Media changes were performed on the cells every third day assuming day of plating is day 0 using emSBM containing EGF. Primary cultures take from 7–17 days to become confluent at which time cells can be further serially cultured as described in Example 2, below, or frozen down and stored in liquid nitrogen for later use. Freeze medium contains LCDMEM as a base with 10% fetal bovine serum and 10% dimethylsufoxide (DMSO). To freeze, cells are removed from the dish and counted the same as in Example 2, but after counting, spun down again and resuspended in freeze medium at between $2 \times 10^6$ and $5 \times 10^6/ml$ and aliquoted into 1.8 ml nunc cryovials. After an 18–24 hour prefreeze, vials are transferred to a liquid nitrogen storage tank until needed. The results of these experiments are reported in Table 1, below. Cell viability was normally in excess of 90%.

The abbreviations used in Table 1 have the following meanings: "HEP" indicates human epidermal cells; "n" indicates neonatal foreskin cells; "NF" followed by a number indicates human epidermal cells from a source other than foreskin.

TABLE 1

Establishment of Primary Cultures using Enhanced mSBM

| Strain HEP | Age of Donor | Mixed Cell Inoculum From Whole Tissue | Inoculum Density | Primary Keratinocyte Yield | Approx* No. of Generations | Days |
|---|---|---|---|---|---|---|
| B036 | n | $1.6 \times 10^7$ | $2.5 \times 10^4/cm^2$ | $3.5 \times 10^7$ | 8.8 | 16 |
| B037 | n | $1.0 \times 10^7$ | $2.5 \times 10^4/cm 2$ | $3.1 \times 10^7$ | 9.3 | 8 |
| B038 | n | $1.6 \times 10^7$ | $2.5 \times 10^4/cm 2$ | $1.2 \times 10^8$ | 10.6 | 12 |
| B040 | n | $6 \times 10^6$ | $2.5 \times 10^4/cm 2$ | $3.0 \times 10^7$ | 10.0 | 8 |
| B041 | n | $1.0 \times 10^7$ | $2.5 \times 10^4/cm 2$ | $1.1 \times 10^7$ | 7.8 | 16 |
| B042 | n | $1.4 \times 10^7$ | $2.5 \times 10^4/cm 2$ | $6.0 \times 10^6$ | 6.5 | 8 |
| B043 | n | $1.5 \times 10^7$ | $2.5 \times 10^4/cm 2$ | $1.2 \times 10^7$ | 7.9 | 8 |
| B044 | n | $1.4 \times 10^7$ | $2.5 \times 10^4/cm 2$ | $1.2 \times 10^7$ | 7.5 | 8 |
| B045 | n | $1.4 \times 10^7$ | $2.5 \times 10^4/cm 2$ | $8.2 \times 10^6$ | 6.9 | 16 |
| NF100 | 2 yr | $1.8 \times 10^6$ | | $4.25 \times 10^5$ | 5.6 | 7 |
| NF101 | 2 yr | $4.0 \times 10^6$ | | $1.6 \times 10^7$ | 9.6 | 14 |
| NF102 | 6 yr | $4.0 \times 10^5$ | | $9.0 \times 10^6$ | 12.0 | 17 |
| NF103 | 6 yr | $6 \times 10^6$ | | $1.7 \times 10^7$ | 9.1 | 11 |

*Calculated based on average colony forming efficiency of 0.5% for primaries obtained from a mixed cell digest.

EXAMPLE 2

Effect of Serial Passage of Colony Forming Efficiency ("CFE") and Growth Rate

Human epidermal cells in T75 flasks obtained as in Example 1 above, were placed in a vertical laminar flow hood and the media was aspirated off and replaced with 2 ml/60 mm dish or 5 ml/T75 of trypsin versene (200 mg versene (EDTA) and 500 mg trypsin/liter in balanced salt solution (without calcium or magnesium, M.A. Bioproducts). Flasks were incubated at 37° C. for about three minutes or until cells came off the surface of the dish. Then, 2 ml/60 mm dish or 5 ml/T75 of soybean trypsin inhibitor (2.5 mg/ml in phosphate buffered saline, GIBCO) was added. Using a pipette, the surface of the flasks, where the cells were growing was sprayed to rinse any adhering cells off. The cell suspension was pipetted into a tube and spun for five minutes at 1200 rpm. The supernate was aspirated off, leaving only the cell pellet. The pellet was resuspended in a convenient volume of mSBM without EGF for counting (Usually 5 ml suffices). After counting cells, 8833 cells/cm$^2$ ($25 \times 10^5/60$ mm dish) were seeded with a final volume of 4 mls/60 mm dish using mSBM without EGF. Cells were incubated at 37° C. in 10% CO2. After 24 h EGF was added to 10 ng/ml. The media was replaced every third day with fresh media (including EGF) assuming day of plating is day 0. Cells became confluent in 5–7 days and at this point were subpassaged again.

Keratinocytes cultured in mSBM are highly mobile, forming diffuse colonies; therefore, colony forming efficiency is approximated as plating efficiency. Plating efficiencies as determined by cell counts 24 hours post seeding were routinely 30% to 35% at low passage (P:3 or P:4), while 100% plating efficiences or greater were frequently observed at 24 hours (Table 2), perhaps due to a particularly short lag phase at this stage.

Keratinocytes obtained from newborn human foreskins (strains FS16, BO09 and B013, Table 2) maintained a population of primarily small round cells (shown by other investigators to represent a rapidly proliferating culture) through passage 6 (greater than 25 population doublings or 6,400 to 333,000 fold increase in cell number). Similarly, keratinocytes from a 2 year old donor were maintained through passage 6 for greater than 24 population doublings or approximately a 4,600 fold increase in cell number.

TABLE 2

| CELL STRAIN | PASSAGE NUMBER | TOTAL POPULATION DOUBLINGS | POPULATION DOUBLINGS PER DAY | PERCENT PLATING EFFICIENCY |
|---|---|---|---|---|
| FS16 | 1 | — | — | — |
| | 2 | 12.8[a] | 0.75[c] | — |
| | 3 | 16.7 | 1.99 | — |
| | 4 | 24.5 | 0.97 | 106 ± 3 |
| | 5 | 29.2 | 1.57 | 41 ± 7 |
| | 6 | 33.3 | 0.59 | — |
| B009 | 1 | 10.7 | 0.82 | — |
| | 2 | 15.7 | 1.26 | 76 ± 8 |
| | 3 | 21.2 | 1.37 | 125 ± 11 |
| | 4 | 25.4 | 0.84 | 100 |
| B013 | 1 | —[b] | — | — |
| | 2 | 4.8 | 0.81 | — |
| | 3 | 10.7 | 1.48 | — |
| | 4 | 15.6 | 0.69 | 29 ± 6 |
| | 5 | 21.1 | 0.42 | 32 ± 1 |
| | 6 | 27.1 | 0.75 | 30 |
| TNF 100 (2 YEAR OLD) DONOR) | 1 | 5.6 | 0.80 | |
| | 2 | 9.1 | 0.39 | |
| | 3 | 12.4 | 0.55 | |
| | 4 | 16.0 | 0.51 | |
| | 5 | 20.3 | 0.86 | |
| | 6 | 24.4 | 0.65 | |

[a] Total combined P:1 and P:2.
[b] Cells from tissue explants, number of doublings cannot be determined.
[c] Passage 1 and 2 combined average.

EXAMPLE 3

Effect of Calcium Concentration

Human keratinocytes were cultivated in mSBM (0.08 mM calcium) or mSBM plus 1.8 mm $Ca^{++}$ at both 0.3% and 1.0% serum in accordance with the procedures described above. Addition of calcium to the medium resulted in a change in morphology. When high calcium was present cells grew in tightly packed colonies while still maintaining a high proportion of small, proliferative cells. No appreciable diminution of growth rate was observed if the serum concentration was kept below 1%. Cell yields at confluence are significantly higher in the plus calcium cells due to the stratification allowed by the high calcium.

The ability to vary the calcium concentration while maintaining a proliferative culture allows experiments to be performed which previously were not possible, such as studying the effects of growth factors and their induction of differentiation, proliferation or growth inhibition as it relates to calcium, a known inducer of terminal differentiation in competent cells. An example of such an experiment is shown in Table 3 where the effects of TGFβ as it relates to calcium was studied. It was observed that the effect of TGFβ is reversible even in the presence of calcium.

TABLE 3

| Condition[c] | EXPT. 1 cell # ; % env[a] | EXPT. 2 cell # ; % env |
|---|---|---|
| (+)T, (+)$Ca^{++}$ | $6.5 \times 10^4$; 6% | $5.0 \times 10^4$; 12% |
| | $6.3 \times 10^4$; 6% | $5.3 \times 10^4$; 10% |
| (−)T, (−)$Ca^{++}$ | $5.3 \times 10^5$; 15% | $4.1 \times 10^5$; 38% |
| | $5.8 \times 10^5$; 18% | $4.3 \times 10^{5; 39\%}$ |
| (−)T, (+)$Ca^{++}$ | $6.5 \times 10^5$; 45% | $3.8 \times 10^5$; 49% |
| | $6.7 \times 10^5$; 47% | $3.6 \times 10^5$; 51% |
| (+)T, (−)$Ca^{++}$ | $3.1 \times 10^5$; 3% | $7.5 \times 10^4$; 5% |
| | $3.2 \times 10^5$; 5% | $7.3 \times 10^4$; 5% |
| (+)T, (+)Ca++b | $3.5 \times 10^5$; 43% | $1.3 \times 10^5$; 40% |
| | $2.6 \times 10^5$; 30% | $2.0 \times 10^5$; 45% |
| (+)T, (−)$Ca^{++b}$ | $7.5 \times 10^5$; 80% | $2.4 \times 10^{5; 100\%}$ |
| removed, 48 h | $7.7 \times 10^5$; 99% | $4.8 \times 10^5$; 73% |

Table represents data from 2 separate experiments showing the effects of calcium and TGFβ on human keratinocytes in mSBM.
a) % env = % ionophore induced envelopes
b) Calcium and TGBβ were removed and cells cultivated for an additional 48 hrs in mSBM to show recovery of cells. Note: the differences in % induced envelopes indicating an effect of TGFβ treatment ± $Ca^{++}$ not related to growth.
c) The media contained 0.3% cFBS; 5 ng/ml TGFβ was added where indicated ((+) T); 1.8 mM calcium was added where indicated ((+) $Ca^{++}$).

EXAMPLE 4

Effect of Serum Concentration

Human epidermal cells (HEP) were plated $1.7 \times 10^5$ cells/ 28.3 $cm^2$ in collagen coated tissue culture dishes in mSBM using various concentrations of chelexed Fetal Bovine Serum (cFBS) and cultured as described herein above. 24 hour plating effeciencies, final cell yields, % of cells in the 9–14 nM diameter range (known to be the small, proliferative cell population, Barrandon and Green, supra) were measured and are reported in Table 4 below. Although increased serum concentration did not significantly influence final cell yields, it increased plating efficiency to a small degree. There was however a reduction in the percentage of small proliferative cells with increased serum concentration. This change in cell population could also be seen by phase contrast microscopy.

TABLE 4

| | 24HR (%) PLATING | FINAL | CELLS % |
|---|---|---|---|
| % cFBS | EFFICIENCY | CELL YIELD | 9–14 nM diameter |
| 0 | 50.8 ± 3.8 | $2.1 \times 10^6 \pm 0.5$ | 42.4 ± 0.9 |
| 0.1 | 51.4 ± 2.1 | $2.8 \times 10^6 \pm 0.3$ | 41.8 ± 0.2 |
| 0.3 | 53.3 ± 1.7 | $2.8 \times 10^6 \pm 0.2$ | 39.3 ± 0.3 |
| 0.5 | 52.0 ± 5.1 | $2.8 \times 10^6 \pm 0.2$ | 34.8 ± 0.2 |
| 1.0 | 57.4 ± 1.7 | $2.1 \times 10^6 \pm 0.3$ | 34.4 ± 2.3 |

Cells may be grown in mSBM and emSBM at various serum concentrations ranging from serum free to serum concentrations of 5% or higher. However, serum is found to promote terminal differentiation or aging of the cell population as evidenced by the distinct loss of cells in the 9–14 mM range even with an increase of serum to only 1%. This is in spite of the fact that calcium has been removed from the serum by chelexing. These findings provide further evidence that serum contains factors which either directly or indirectly affect cell proliferation and differentiation and which are unrelated to calcium.

EXAMPLE 5

Effect of Substrate

A substrate of either Type I collagen or fibronectin has been found to be beneficial in establishing epidermal cells as primaries and from frozen stocks using either mSBM or emSBM. Collagen is routinely used in the cultivation of human epidermal keratinocytes using mSBM. However, a study was carried out to determine actual substrate dependence and the effect of substrate over culture lifespan.

Frozen stocks, of human epidermal keratinocytes developed as primaries in emSBM using a collagen substrate, were plated on dishes, in accordance with procedures described herein above, both with (+CN) and without collagen (−CN) and grown in mSBM. At confluence, both the +CN cells were passed onto dishes with and without collagen (See Table 5A) and the −CN cells were passed onto dishes both with and without collagen (See Table 5B). General morphology, 4 hr plating efficiency and cell size distribution were examined at each passage. Plating efficiencies in excess of 100% are indicative of the unusually short lag period before reinitiation of growth that occurs when keratinocytes are passaged in the claimed media. Cells from either condition were plated and harvested concurrently where direct comparisons are made in the Tables. The percentages of cells of 9–14 mM diameter are indicative of the % of undifferentiated, proliferative cells in the population (Barrandon and Green, supra).

Cells established from frozen primary cultures without collagen showed a slight decrease in plating efficiency over those plated on collagen. As the cells without collagen (−CN) were passed further onto dishes with (+CN) or without (−CN), the plating efficiency was consistently better in the (+CN) condition. However, −CN grown cells were able to grow to confluence and be passaged (See Table 5B).

Cells maintained with collagen and then passed onto dishes with or without collagen showed variable plating efficiencies with no clear advantage or disadvantage to using or not using collagen for the subsequent passage (See Table 5A).

Cells grown and passed onto collagen through passage 8 showed a drop in plating efficiency at passage 8 (equivalent to approx. 29.4 population doublings). Cells grown in the absence of collagen showed a drop in plating efficiency between p6 and p7 (equivalent to approx. 19–22 population doublings).

A strain of epidermal cells established in high serum (5%) with 3T3 feeder cells (See, e.g., Rheinwald and Green, supra), were plated at p4 from frozen stocks onto dishes with or without collagen and showed no significant difference in plating efficiency. Furthermore, it was observed that significantly lower plating efficiencies were obtained in this experiment than when using mSBM-grown cells (See Tables 5A and 5B).

Collagen did not appear to influence the percentage of the cell population falling in the 9–14 mm diameter range, i.e., the proliferative cell population through passage 7 (–CN) or passage 8 (+CN) (See Table 5C).

TABLE 5

PLATING EFFICIENIES FOR +/– COLLAGEN EXPERIMENT

TABLE 5A: PLATING EFFICIENCIES OF +CN/–CN UPON PASSAGE OF +CN CONDITION

|  |  |  |  | AVE. | % of Cells Bet.9–14 mm |
|---|---|---|---|---|---|
| +CN P2 | 100 | 75 | 75 | 83.3 | 66% |
| –CN P2 | 38 | 50 | 75 | 54.3 | 52% |
| +CN P3 | 50 | 50 | 50 | 50 | 71% |
| –CN P3 | 19 | 15 | 16 | 16.7 | 30% |
| +CN P4 | 90 | 105 | 115 | 103.3 | 44% |
| –CN P4 | 85 | 110 | 105 | 101.6 | 37% |
| +CN P5 | 55 | 57.5 | 62.7 | 58.3 | 54% |
| –CN P5 | 130 | 100 | 65 | 98.3 | 66% |
| +CN P6 | 160 | 140 | 120 | 140 | 12% |
| –CN P6 | 100 | 130 | 110 | 13.3 | 13% |
| +CN P7 | 80 | 75 | 70 | 75 | 14% |
| –CN P7 | 65 | 75 | 95 | 78.3 | 14% |
| +CN P8 | 32 | 41 | 33 | 35.6 | 43% |
| –CN P8 | 32 | 34 | 33 | 33 | 43% |

TABLE 5B: PLATING EFFICIENCIES OF +CN/–CN UPON PASSAGE OF –CN CONDITION

|  |  |  |  | AVE. | % of Cells Bet.9–14 mm |
|---|---|---|---|---|---|
| –CN P2 | 38 | 50 | 75 | 54.3 | 52% |
| +CN P3 | 160 | 155 | 188 | 167.6 |  |
| –CN P3 | 68 | 83 | 80 | 77 | 42% |
| +CN P4 | 50 | 45 | 70 | 55 | 21% |
| –CN P4 | 18 | 18 | 20 | 18.7 | 38.5% |
| +CN P5 | 120 | 120 | 80 | 106.7 | 8.5% |
| –CN P5 | 80 | 120 | 100 | 100 | 11.6% |
| +CN P6 | 75 | 86 | 45 | 68.7 | 16% |
| –CN P6 | 25 | 35 | 35 | 31.6 | 18% |
| +CN P7 | 25 | 32 | 30 | 29 | 33.6% |
| –CN P7 | 22 | 23 | 20 | 21.6 | 32% |

TABLE 5C: HEP 026-7 P4 PLATING EFFICIENCIES

| +CN P4 | 8 | 12 | 13 | 11 | — |
|---|---|---|---|---|---|
| –CN | 11 | 12 | 9 | 10.6 | — |

EXAMPLE 6

Fabrication of Living Skin Equivalents and Keratinocyte Sheets

Living skin equivalents were fabricated using mSBM-grown keratinocytes in high serum (5%) and high calcium (1.8 mM). It should be noted that this can't be done using MCDB 153 grown keratinocytes. The epidermis developed normally, with stratification and differentiation, while still maintaining a basal layer.

A Living Skin Equivalent was fabricated using keratinocytes grown in mSBM plated onto a dermal equivalent made according to established procedures (See, e.g., the Patents. The skin equivalent was then allowed to grow in mSBM for 2 days after which $Ca^{++}$ was added to allow stratification. Continued culture of the skin equivalent in mSBM, 0.3% cFBS and $Ca^{++}$ yielded a well organized differentiating epidermal layer.

Sheets of stratified epidermal cells suitable for grafting, etc. have also been fabricated by establishment of cells in mSBM on collagen, increasing the calcium concentration to 1.8 mM at confluence, maintaining 4 days with daily feeding using mSBM with 1.8 mm $Ca^{++}$ followed by removal of the coherent cell sheet using collagenase.

EXAMPLE 7

Large Scale Cultivation of Keratinocytes Using Collagen-Coated Microcarriers

Human epidermal keratinocytes have been successfully plated onto collagen coated cross-linked gelatin microcarriers with high efficiency using mSBM medium having a calcium concentration of 0.08 mm and BHE at a concentration of 50 µg/ml. Using a 250 ml Belco culture vessel at 30 rpm with intermittent (2 min. on, 8 min. off) stirring, the seeding of $5.1 \times 10^6$ Human Epidermal Keratinocytes (HEPs) was accomplished with high efficiency (>50%) within a small volume of medium (75 ml) containing 0.5 g of gelibeads. The gelibeads were prepared as follows: equilibration with mSBM following coating with approximately 9.5 mg of bovine tendon collagen overnight in 100 ml of pure water, and subsequent rinsing first with phosphate buffered saline, followed by calcium free DMEM. After 1 week, confluent beads were harvested with trypsin-EDTA and $2.1 \times 10^7$ cells were yielded. These cells, when plated with standard culture conditions and mSBM into T25 cultured flasks, were found to have a plating efficiency in excess of 100% as determined by harvesting and counting 24 hrs. later.

This procedure was repeated using a keratinocyte cell strain designated HEp 047 at passage 5. Cells were plated at $6 \times 10^6$ into each of two spinner flasks containing 0.25 grams of gelibeads (about 1000 cm² of surface area) in 150 ml of medium. The cell yields from the two flasks after 6 days were $6.2 \times 10^7$ and $5.8 \times 10^7$. Thus, an average ten fold increase in cell number was achieved.

Another experiment demonstrated the efficacy of bead-to-bead transfer of cells for ease of passage without the use of a protease. A cell strain designated HEp 038 at passage 4 were plated onto spherical collagen coated gelibeads. Irregularly shaped collagen coated gelatin beads were then added to the culture after 4 days. The beads were examined microscopically after 2 additional days. Cells were seen attached to both the spherical gelibeads and the irregularly shaped gelatin beads.

EXAMPLE 8

The Addition of Divalent Cation Sustitutes for Calcium in mSBM

Strontium at 1 mM and magnesium at 3 mM were compared in mSBM +/– Bovine Hypothalamic Extract for improvements in cell growth and size distribution in human epidermal keratinocytes at passage 4. The table below sets forth the results from triplicate cultures.

| Cation | −BHE Cell # (pdt) | +BHE Cell # (pdt) | −BHE %9–14 um | +BHE %9–14 um |
|---|---|---|---|---|
| NONE | $9.03 \times 10^5 \pm 0.18(27.5h)$ | $9.22 \times 10^5 \pm 0.79(27.3h)$ | $22.3 \pm 1.8$ | $27.2 \pm 1.0$ |
| Mg | $8.2 \times 10^5 \pm 0.14(28.2h)$ | $9.10 \times 10^5 0.32(27.4h)$ | $19.5 \pm 1.0$ | $24.0 \pm 0.9$ |
| Sr | $13.9 \times 10^5 \pm 0.79(24.6h)$ | $15.5 \times 10^5 \pm 0.38(23.9h)$ | $24.5 \pm 0.4$ | $26.2 \pm 0.7$ |

A strontium dose response was also determined for a different stain of keratinocytes. 1 mM Sr was found to increase cell yield from $1.7 \times 10^6$ to $2.1 \times 10^6$. The 9–14 um distribution was increased from 20% to 26%. In a separate experiment, yet another strain showed an improvement in cell yield from $1.45 \times 10^6$ to $2.66 \times 10^6$ with 1 mM Sr and a doubling time reduction from 33.9 to 28.1 hours.

EXAMPLE 9

Establishment of Primary Cultures in mSBM Using Explant Outgrowth

Primary explant cultures were established using the following modified mSBM formulation:

| | |
|---|---|
| Hydrocortisone | 1.1 uM |
| Insulin | 5 ug/ml |
| Transferrin | 5 ug/ml |
| Triiodothyronine | 20 pM |
| Ethanolamine | $1 \times 10^{-4}$ M |
| O-phosphorylethanolamine | $1 \times 10^{-4}$ M |
| Adenine | 0.18 mM |
| Selenium | $5.26 \times 10^{-8}$ M |
| Epidermal Growth Factor | 10 ng/ml |
| Ca++-free DMEM | 75% |
| Hams-F-12 | 25% |
| Strontium | 1 mM |

The modification consisted of omitting progesterone (which could act to lower cAMP levels) and cAMP elevating agents, and adding strontium which has been shown to have growth promoting effects in mSBM (See Example 8).

Neonatal foreskin was dissected free of fat and subcutaneous tissue and minced into 1–2 mm² pieces. Explant cultures were established in the above medium with the addition of bovine hypothalamic extract at (50 ug/ml) (BHE), except where noted.

Yields from explant outgrowths are shown in Table 9A.

The cells were then passed into 100 mm diam. culture dishes at $3 \times 10^5$ cells/dish keeping the media conditions constant. Yields from secondary culture (harvested after approximately 1 week) are shown in Table 9B.

TABLE 9A

Establishment of Primary Cultures in mSBM using Explant* Outgrowth.

| Cell Strain | Days in Culture | Primary Yield ($\times 10^6$) |
|---|---|---|
| B049 | 13d. | 19.0 |
| B050 | 13d. | 41.0 |
| B051 | 13d. | 38.0 |
| B052 | 14d. | 4.7 |
| B053 | 14d. | 7.0 |
| B054 | 13d. | 8.2 |
| B055 | 14d. | 30.0 |
| B056 | 14d. | 9.7 |
| B058 | 14d. | 26.0 |
| B059 | 14d. | 16.0 |
| B070 | 11d. | 11.0 |
| B071 | 11d. | 12.0 |
| B075# | 13d. | 23.0 |
| B082# | 12d. | 65.0 |

*Cells were derived from explants of neonatal foreskin. Note that in most cases, the entire foreskin was not utilized for explant culture, a portion of it being reserved for derivation of dermal fibroblast strains.
Strains established without bovine hypothalmic extract (BHE)

TABLE 9B

Growth of Secondary Cultures in mSBM

| Cell Strain | Days in Culture | # of Cells Plated* ($\times 10^6$) | Yield ($\times 10^6$) |
|---|---|---|---|
| B049 | 7d. | 3.0 | 75.0 |
| B050 | 7d. | 9.0 | 250.0 |
| B051 | 7d. | 9.0 | 140.0 |
| B052 | 10d. | 3.0 | 100.0 |
| B055 | 10d. | 12.0 | 220.0 |
| B082# | 6d. | 12.0 | 310.0 |

*Note that only a portion of cells were plated from primary. For example, if all primary keratinocytes from strain B050 were plated as secondaries, the total yield would be $1.14 \times 10^9$ after 21 total days in culture.
Strain established and cultivated without the use of bovine hypothalamic extract (BHE).

EXAMPLE 10

Growth of Normal Human Epidermal Cells from Primaries Without Exogenous cAMP Elevating Agents, Serum or Bovine Hypothalamic Extract.

Human epidermal cells from three different sources were established from outgrowth of skin explants on collagen coated tissue culture dishes in a modification of mSBM base medium lacking progesterone and containing 1 mM $SrCl_2$. Explants were established both with and without cholera toxin, a potent cAMP elevating agent, chelexed newborn calf serum and bovine hypothalamic extract in order to study the effects of these three agents on establishment of primary cultures and subsequent passages.

Cells developed as explant outgrowths in all conditions examined. Cell yield was monitored over seven serial passages in all the conditions. FIGS. 1 and 2 represents the yield/passage calculated as the cell number obtained if all cells of a given condition were passaged. In FIGS. 1 and 2, "S" represents chelexed serum (0.3%); "CT" represent cholera toxin (9 ng/ml); and "BHE" represents bovine hypothalamic extract (50 µg/ml).

It was observed that neither serum, cholera toxin nor bovine hypothalamic extract were required for establishment of primaries and for the serial passage of normal human keratinocytes. Control cultures lacking these three agents gave a yield of $1 \times 10^{10}$ after only 34 days of cultivation and six serial passages. The control condition also showed improved growth over cultures established and grown in the presence of serum alone and serum with cholera toxin.

While either bovine hypothalamic extract or cholera toxin used without serum were able to increase the final cell yield, bovine hypothalamic extract was able to improve the cell yield to a greater extent as well as to increase the number of passages during which the population doubling rate remained linear. In addition, bovine hypothalamic extract was shown to counterbalance the negative effects of serum to a much greater extent than cholera toxin. Cholera toxin did not appear to have any beneficial effect if bovine hypothalamic extract was present with or without serum.

Thus, neither serum, bovine hypothalamic extract nor cyclic AMP elevating agents are required for establishment and serial passage of human keratinocytes.

EXAMPLE 11

Culture and Passage Without EGF

Keratinocytes designated B063 were established and grown in the mSBM formulation of example 9 with BHE and subsequently frozen for storage at the end of passage 2. These cells were thawed and seeded in 60 mm dishes at $1 \times 10^5$/dish in the above medium without BHE. Half the dishes received EGF to 10 ng/ml two hours post seeding. The cells were harvested and counted at the end of passage 3 and those grown without EGF were replated and again grown to confluence. The data (table 11) show that, if desired, keratinocytes can be grown in mSBM without EGF and, in some instances, growth is comparable to that seen with EGF.

TABLE 11

Effect of EGF on cell yield of HEp B063.

| PASSAGE NUMBER 3 | PASSAGE NUMBER 4 |
| --- | --- |
| +EGF $1.14 \times 10^6$ +/− 0.26 | $2.10 \times 10^6$ +/− 0.23 |
| −EGF $1.6 \times 10^6$ +/− 0.21 | $1.83 \times 10^6$ +/− 1.10 |

EXAMPLE 12

Growth in the Absence of Hydrocortisone

When minimal supplementation is desired hydrocortisone is not required, and its absence may then be preferred.

This was demonstrated by seeeding passage 3 strain B063 keratinocytes at $1.7 \times 10^5$/60 mm dish in the medium of Example 9 with either 0, 0.04, 0.2, 0.4, or 0.8 ug/ml hydrocortisone. Plates were harvested after 24 hours to determine the average plating efficiency and then again at 5 days to determine the growth rate. Cell yields were comparable in all conditions. Doubling times were calculated for the four days between these two determinations (table 12).

TABLE 12

Effect of Hydrocortisone on Passage 3 B063 Keratinocytes

| Hydrocortisone | 0 | 0.04 ug/ml | 0.2 ug/ml | 0.4 ug/ml | 0.8 ug/ml |
| --- | --- | --- | --- | --- | --- |
| Doubling Time | 23.8 hr. | 24.0 hr. | 24.4 hr. | 24.0 hr. | 24.0 hr. |

It is understood that the examples and embodiments described herein are for illustrative purposes only and that various modifications or changes in light thereof that will be suggested to persons skilled in the art are to be included in the spirit and purview of this application and the scope of the approved claims.

What is claimed is:

1. A chemically defined cell culture medium comprising, insulin or an insulin-like growth factor; transferrin or ferrous ion; triiodothyronine or thyroxin; at least one ethanolamine or o-phosphoryl-ethanolamine; calcium; and a nutrient source in the absence of undefined components, wherein:

(a) Insulin is present at from about 0.5 to about 50 µg/ml or an insulin-like growth factor is present at from about $10^{-10}$ to about $10^{-8}$M;

(b) Transferrin is present at from about 0.05 to about 50 µg/ml or ferrous ion is present at from about $5 \times 10^{-8}$ to about $5 \times 10^{-5}$M;

(c) Triiodothyronine is present at from about 2 to about 200 pM;

(d) At least one of o-phosphoryl-ethanolamine and ethanolamine is present at from about $10^{-6}$ to about $10^{-2}$M;

(e) Calcium is present at from about 0.005 to about 2.0 mM; and (f) Nutrient source is selected from at least one of DMEM, IDMEM, MEM, M199, RPMI 1640, Ham's F12, Ham's F10, NCTC 109, and NCTC 135.

2. The cell culture medium of claim 1, further comprising hydrocortisone.

3. The cell culture medium of claim 2, wherein hydrocortisone is present at from about 0.04 to about 4.0 ug/ml.

4. The cell culture medium of claim 1, further comprising epidermal growth factor.

5. The cell culture medium of claim 4, wherein epidermal growth factor is present at from about 1 to about 50 ng/ml.

6. The cell culture medium of claim 1, further comprising a cyclic AMP elevating agent.

7. The cell culture medium of claim 6, wherein the cyclic AMP elevating agent is present at from about $10^{-9}$ to about $10^{-3}$M.

8. The cell culture medium of claim 1, wherein the cyclic AMP elevating agent is selected from at least one of cholera toxin, foreskolin, isoproterenol, methyl isobutyl xanthine, dibutryrl cyclic AMP, theophylline, caffeine and pertussis toxin.

9. The cell culture medium of claim 1, further comprising adenine at from about 0.02 to about 2.0 mM.

10. The cell culture medium of claim 1, further comprising progesterone at from about $2 \times 10^{-10}$ to about $2 \times 10^{-8}$M.

11. The cell culture medium of claim 1, further comprising selenium from about $10^{-9}$ to about $10^{-7}$M.

12. The cell culture medium of claim 1, further comprising at least one of the group consisting of acidic fibroblast growth factor, basic fibroblast growth factor, and keratinocyte growth factor, wherein the growth factor is present at about $10^{-10}$ to about $10^{-6}$ g/ml.

13. The cell culture medium of claim 1, further comprising EGF at from about 1 to about 50 ng/ml.

14. The cell culture medium of claim 1, wherein the medium is for the culture of epithelial cells.

15. The cell culture medium of claim 1, wherein the medium is for the culture of keratinocyte cells.

16. The cell culture medium of claim 1, wherein the nutrient source is 75% calcium free DMEM and 25% Ham's F12.

17. A method of epidermalizing a dermis comprising:

a) inoculating a living tissue equivalent with epidermal cells;

b) maintaining the living tissue equivalent of step a) in a cell culture medium in accordance with claim 1 and under conditions to promote development of an epidermis; and c) adding calcium to bring the medium to about physiological concentration and maintaining the living tissue equivalent of step b) under conditions to allow stratification of the epidermis.

18. A method of culturing epithelial cells comprising, inoculating a medium in accordance with claim 1 with the epithelial cells, and maintaining the cells and medium under conditions to promote cell growth.

19. Epithelial cells produced in accordance with the method of claim 18.

20. A cell culture system comprising the chemically defined cell culture medium of claim 1, and a substrate for the cells, wherein the substrate for the cells is selected from the group consisting of plastic, glass, collagen, fibronectin, laminin, heparan sulfate proteoglycan, a living tissue equivalent, and a microcarrier, wherein the microcarrier is coated with collagen, fibronectin, laminin or heparan sulfate proteoglycan.

21. The cell culture system of claim 20, wherein the collagen is native Type I collagen derived from bovine tendon.

22. A method of culturing epithelial cells comprising, providing epithelial cells to the substrate of the cell culture system of claim 20, and maintaining the cell culture system under conditions to promote cell growth.

23. Epithelial cells produced in accordance with the method of claim 22.

24. A method of producing keratinocytes comprising the steps of:

a. plating a substrate in a cell culture system in accordance with claim 20 with keratinocytes;

b. maintaining the substrate of step a. under conditions to promote cell growth; and c. adding calcium to the medium to physiological concentration and maintaining the substrate of step b. under conditions to allow stratification of the keratinocytes.

25. A method of producing keratinocytes in accordance with claim 24 wherein the substrate is flat and the keratinocytes form a sheet on the substrate.

26. A method of producing a sheet of keratinocytes comprising enzymatically detaching a sheet of keratinocytes prepared in accordance with claim 25.

27. Keratinocytes produced in accordance with the method of claim 24, 26 or 25.

* * * * *